(12) United States Patent
Fujita et al.

(10) Patent No.: US 10,660,317 B2
(45) Date of Patent: May 26, 2020

(54) GENETICALLY MODIFIED NON-HUMAN MAMMALS AND CELLS

(71) Applicant: University of Leicester, Leicester (GB)

(72) Inventors: Teizo Fujita, Fukushima (JP); Hans-Wilhelm Schwaeble, Mountsorrel (GB); Cordula Margaret Stover, Wigston Meadows (GB)

(73) Assignee: University of Leicester, Leicester (GB)

( * ) Notice: Subject to any disclaimer, the term of this patent is extended or adjusted under 35 U.S.C. 154(b) by 0 days.

(21) Appl. No.: 15/348,162

(22) Filed: Nov. 10, 2016

(65) Prior Publication Data

US 2017/0127657 A1 May 11, 2017

Related U.S. Application Data

(60) Continuation of application No. 14/316,235, filed on Jun. 26, 2014, now abandoned, which is a division of application No. 11/570,087, filed as application No. PCT/GB2005/050086 on Jun. 8, 2005, now Pat. No. 8,785,717.

(30) Foreign Application Priority Data

Jun. 10, 2004 (GB) .................................. 0412966.4

(51) Int. Cl.
| | | |
|---|---|---|
| *A01K 67/00* | (2006.01) | |
| *C12N 15/85* | (2006.01) | |
| *A01K 67/027* | (2006.01) | |
| *C12N 9/64* | (2006.01) | |
| *C07K 16/28* | (2006.01) | |
| *C07K 16/40* | (2006.01) | |
| *A61K 38/00* | (2006.01) | |

(52) U.S. Cl.
CPC ...... *A01K 67/0278* (2013.01); *A01K 67/0276* (2013.01); *C07K 16/2851* (2013.01); *C07K 16/40* (2013.01); *C12N 9/6424* (2013.01); *C12N 15/8509* (2013.01); *A01K 2207/15* (2013.01); *A01K 2217/00* (2013.01); *A01K 2217/072* (2013.01); *A01K 2217/075* (2013.01); *A01K 2227/105* (2013.01); *A01K 2267/01* (2013.01); *A01K 2267/03* (2013.01); *A61K 38/00* (2013.01); *C07K 2317/14* (2013.01); *C12N 2510/00* (2013.01); *C12N 2517/00* (2013.01); *C12N 2800/30* (2013.01)

(58) Field of Classification Search
CPC .... C07K 16/40; C07K 16/2851; C07K 16/04; C12N 15/8509; C12N 9/6424; A01K 67/0278; A01K 67/0276; A01K 2207/15; A01K 2217/00; A01K 2217/072; A01K 2217/075; A01K 2227/105; A01K 2267/01; A01K 2267/03; A61K 38/00; A61K 9/0024; A61K 47/10; A61K 47/34

See application file for complete search history.

(56) References Cited

U.S. PATENT DOCUMENTS

| | | | |
|---|---|---|---|
| 4,331,647 | A | 5/1982 | Goldenberg et al. |
| 4,816,567 | A | 3/1989 | Cabilly et al. |
| 4,946,778 | A | 8/1990 | Ladner et al. |
| 5,464,764 | A | 11/1995 | Capecchi et al. |
| 5,693,762 | A | 12/1997 | Queen et al. |
| 6,969,601 | B2 | 11/2005 | Jensenius et al. |
| 7,060,267 | B2 | 6/2006 | Jensenius et al. |
| 7,083,786 | B2 | 8/2006 | Jensenius et al. |
| 7,112,414 | B2 | 9/2006 | Jensenius et al. |
| 2002/0082208 | A1 | 6/2002 | Jensenius et al. |
| 2002/0082209 | A1 | 6/2002 | Jensenius et al. |
| 2002/0094332 | A1 | 7/2002 | Bell |
| 2003/0049260 | A1 | 3/2003 | Bell |
| 2003/0207309 | A1 | 11/2003 | Hageman et al. |
| 2004/0038297 | A1 | 2/2004 | Jensenius et al. |
| 2004/0081619 | A1 | 4/2004 | Bell |
| 2004/0219147 | A1 | 11/2004 | Bell et al. |
| 2004/0259771 | A1 | 12/2004 | Stahl et al. |
| 2005/0004031 | A1 | 1/2005 | Subasinghe et al. |
| 2005/0222027 | A1 | 10/2005 | Chiang et al. |
| 2006/0002937 | A1 | 1/2006 | Schwaeble et al. |
| 2006/0018896 | A1 | 1/2006 | Schwaeble et al. |
| 2006/0275764 | A1 | 12/2006 | Thiel et al. |
| 2007/0009528 | A1 | 1/2007 | Larsen et al. |
| 2007/0031420 | A1 | 2/2007 | Jensenius et al. |

FOREIGN PATENT DOCUMENTS

| | | |
|---|---|---|
| WO | WO 91/11465 | 8/1991 |
| WO | WO 00/35483 | 6/2000 |
| WO | WO 01/12212 | 2/2001 |
| WO | WO 02/06460 | 1/2002 |

(Continued)

OTHER PUBLICATIONS

Costagliola et al 1998, 160:1548-1465.*
Thiel et al., 2000, J. Immunol 165:878-887.*
Swarthout et al., Zinc Finger Nucleases: A new era for transgenic animals Annals of Neurosciences, pp. 25-28.*
Swarthout et al., 2011 Zinc Finger Nucleases: A new era for transgenic animals Annals of Neurosciences, pp. 25-28.*
Chen, C.B., et al., "Stoichiometry of complexes between mannose-binding protein and its associated serine proteases. Defining functional units for complement activation," *J. Bio. Chem.* 276(28):25894-25902 (2001).
Feinberg, H., et al., "Crystal structure of the CUB1-EGF-CUB2 region of mannose-binding protein associated serine protease-2," *EMBO J.* 22(10):2348-2359 (2003).

(Continued)

*Primary Examiner* — Maria G Leavitt
(74) *Attorney, Agent, or Firm* — Tineka J. Quinton

(57) ABSTRACT

Genetically modified mammals are described which lack the mannan binding lectin associated serine protease MASP-2, together with methods and constructs for their production. Such mammals are useful as models for disorders of the complement system, and in the identification of treatments for such disorders. Also described are mammals which lack the associated protein MAp19; such mammals may also lack MASP-2.

2 Claims, 15 Drawing Sheets

Specification includes a Sequence Listing.

(56) References Cited

FOREIGN PATENT DOCUMENTS

| WO | WO 03/009803 | 2/2003 |
|---|---|---|
| WO | WO 03/061765 | 7/2003 |
| WO | WO 2004/050907 | 6/2004 |
| WO | WO 2004/106384 | 12/2004 |
| WO | WO 2005/002627 | 1/2005 |
| WO | WO 2005/024013 | 3/2005 |
| WO | WO 2005/123128 | 12/2005 |
| WO | WO 2005/123776 | 12/2005 |

OTHER PUBLICATIONS

Lynch, N. J., et al., "L-ficolin specifically binds to lipoteichoic acid, a cell wall constituent of Gram-positive bacteria, and activates the lectin pathway of complement," *J. Immunol.* 172(2):1198-1202 (2004).
Stover, C.M., et al., "Two constituents of the initiation complex of the mannan-binding lectin activation pathway of complement are encoded by a single structural gene," *J. Immunol.* 162(6):3481-3490 (1999).
Stover, C.M., et al., "The rat and mouse homologues of MASP-2 and MAp19, components of the lectin activation pathway of complement," *J. Immunol.* 163(12):6848-6859 (1999).
Thiel, S., et al., "A second serine protease associated with mannan-binding lectin that activates complement," *Nature* 386:506-510 (1997).
Thiel, S., et al., "Interaction of C1q and mannan-binding lectin (MBL) with C1r, C1s, MBL-associated serine proteases 1 and 2, and the MBL-associated protein MAp19," *J. Immunol.* 165(2):878-887 (2000).
Vorup-Jensen, T., et al., "Distinct pathways of mannan-binding lectin (MBL)- and C1-complex autoactivation revealed by reconstitution of MBL with recombinant MBL-associated serine protease-2," *J. Immunol.* 165(4):2093-2100 (2000).
Thielens, N.M., et al., "Interaction properties of human mannan-binding lectin (MBL)-associated serine proteases-1 and -2, MBL-associated protein 19, and MBL," *J. Immunol.* 166(8):5068-5077 (2001).
Matsushita, M., et al., "Cutting edge: complement-activating complex of ficolin and mannose-binding lectin-associated serine protease," *J. Immunol.* 164:2281-2284 (2000).
Matsushita, M., et al., "Proteolytic activities of two types of mannose-binding lectin-associated serine protease," *J. Immunol.* 165:2637-2642 (2000).
Fitch, J.C., et al., "Pharmacology and biological efficacy of a recombinant, humanized, single-chain antibody C5 complement inhibitor in patients undergoing coronary artery bypass graft surgery with cardiopulmonary bypass," *Circulation* 100(25):2499-2506 (1999).
Lachmann, P.J., et al., "Initiation of complement activation," *Springer Semin. Immunopathol.* 7(2-3):143-162 (1984).
Riedemann, N.C., et al., "Complement in ischemia reperfusion injury," *Am. J. Pathol.* 162(2):363-367 (2003).
Matsushita, M., et al., "Activation of the lectin complement pathway by H-ficolin (Hakata antigen)," *J. Immunol.* 168(7):3502-3506 (2002).
Stengaard-Pedersen, K., et al., "Inherited deficiency of mannan-binding lectin-associated serine protease 2," *N. Engl. J. Med.* 349(6):554-560 (2003).
Takahashi, M., et al., "A truncated form of mannose-binding lectin-associated serine protease (MASP)-2 expressed by alternative polyadenylation is a component of the lectin complement pathway," *Int. Immunol.* 11(5):859-863 (1999).
Ambrus, G., et al., "Natural substrates and inhibitors of mannan-binding lectin-associated serine protease-1 and -2: a study on recombinant catalytic fragments," *J. Immunol.* 170(3):1374-1382 (2003).
Moller-Kristensen, M., et al., "Levels of mannan-binding lectin-associated serine protease-2 in healthy individuals," *J. Immunol. Methods* 282(1-2):159-167 (2003).
Petersen, S.V., et al., "Control of the classical and the MBL pathway of complement activation," *Mol. Immunol.* 37(14):803-811 (2000).
Dahl, M.R., et al., "MASP-3 and its association with distinct complexes of the mannan-binding lectin complement activation pathway," *Immunity* 15(1):124-135 (2001).
Petersen, S.V., et al., "An assay for the mannan-binding lectin pathway of complement activation," *J. Immunol. Methods* 257:107-116 (2001).
Collard, C.D., et al., "Complement activation after oxidative stress: role of the lectin complement pathway," *Am. J. Pathol.* 156(5):1549-1556 (2000).
Lu, J., et al., "Collectins and ficolins: sugar pattern recognition molecules of the mammalian innate immune system," *Biochim. Biophys. Acta.*1572(2-3):387-400 (2002).
Jordan, J.E., et al., "Inhibition of mannose-binding lectin reduces postischemic myocardial reperfusion injury," *Circulation* 104(12):1413-1418 (2001).
Maynard, Y., et al., "Characterization of a mannose and N-acetylglucosamine-specific lectin present in rat hepatocytes," *J. Biol. Chem.* 257(7):3788-3794 (1982).
Lee, R.T., et al., "Multivalent ligand binding by serum mannose-binding protein," *Arch. Biochem. Biophys.* 299(1):129-136 (1992).
Collard, C.D., et al., "Endothelial oxidative stress activates the lectin complement pathway: role of cytokeratin 1," *Am. J. Pathol.* 159(3): 1045-1054 (2001).
Ji, Y.H., et al., "Activation of the C4 and C2 components of complement by a proteinase in serum bactericidal factor, Ra reactive factor," *J. Immunol.* 150(2):571-578 (1993).
Kilpatrick, D.C., "Mannan-binding lectin: clinical significance and applications," *Biochim.Biophys.Acta.* 1572(2-3):401-413 (2002).
Weis, W.I., et al., "Structure of a C-type mannose-binding protein complexed with an oligosaccharide,"*Nature* 360:124-134 (1992).
Kalli, K.R., et al., "Therapeutic uses of recombinant complement protein inhibitors," *Springer Semin. Immunopathol.* 15(4):417-431 (1994).
Pangburn, M.K., et al., "Formation of the initial C3 convertase of the alternative complement pathway. Acquisition of C3b-like activities by spontaneous hydrolysis of the putative thioester in native C3," *J. Exp. Med.* 154(3):856-867 (1981).
Wallis, R., et al., "Localization of the serine protease-binding sites in the collagen-like domain of mannose-binding protein: indirect effects of naturally occurring mutations on protease binding and activation," *J. Biol. Chem.* 279(14):14065-14073 (2004).
Jensenius, J.C., et al., "Recombinant mannan-binding lectin (MBL) for therapy," *Biochem. Soc. Trans.* 31:763-767 (2003).
Wallis, R., et al., "Interaction of mannose-binding protein with associated serine proteases: effects of naturally occurring mutations," *J. Biol. Chem.* 275(40):30962-30969 (2000).
Sim, R.B., et al., "Innate Immunity," *Biochemical Society Transactions* 28(5):545-550 (2000).
Petersen, S.V., et al., "Generation of antibodies Towards MASP-1 and MASP-2 Using Bacterial Expression Systems," *Molecular Immunology* 35:409 (1998).
Clackson, T., et al., "Making antibody fragments using phage display libraries," *Nature* 352:624-628 (1991).
Bird, R.E., et al., "Single-chain antigen-binding proteins," *Science* 242:423-426 (1988).
Carter, P., et al., "Humanization of an anti-p185HER2 antibody for human cancer therapy," *Proc. Natl. Acad. Sci. U.S.A.* 89(10):4285-4289 (1992).
Small, J.A., et al., "Analysis of a transgenic mouse containing simian virus 40 and v-myc sequences," *Mol. Cell. Biol.* 5(4):642-648 (1985).
Singer, I.I., et al., "Optimal humanization of 1B4, an anti-CD18 murine monoclonal antibody, is achieved by correct choice of human V-region framework sequences," *J. Immunol.* 150(7):2844-2857 (1993).
Schwaeble, W., et al., "The mannan-binding lectin-associated serine proteases (MASPs) and MAp19: four components of the lectin pathway activation complex encoded by two genes," *Immunobiology* 205(4-5):455-466 (2002).
Sandhu, J.S., "Protein engineering of antibodies," *Crti. Rev. Biotechnol.* 12(5-6):437-462 (1992).

(56) References Cited

OTHER PUBLICATIONS

Porter, R.R., "The hydrolysis of rabbit y-globulin and antibodies with crystalline papain," *Biochem. J.* 73:119-126 (1959).

Presta, L., et al., "Antibody engineering," *Current Opinion in Structual Biology* 2:593-596 (1992).

Pack, P., et al., "Improved bivalent miniantibodies, with identical avidity as whole antibodies, produced by high cell density fermentation of Escherichia coli," *Biotechnology* 11:1271-1277 (1993).

Taylor, L.D., et al., "Human immunoglobulin transgenes undergo rearrangement, somatic mutation and class switching in mice that lack endogenous IgM," *Int. Immunol.* 6(4):579-591 (1994).

Green, L.L., "Antigen-specific human monoclonal antibodies from mice engineered with human Ig heavy and light chain YACs," *Nat. Genet.* 7(1):13-21 (1994).

Matsushita, M., et al., "Activation of the classical complement pathway by mannose-binding protein in association with a novel C1s-like serine protease," *J. Exp. Med.* 176(6):1497-1502 (1992).

Morgan, B.P., et al., "Clinical Complementology: Recent Progress and Future Trends," *Eur.J.Clin.Invest.* 24(4):219-228 (1994).

Ikeda, K., et al., "Serum lectin with known structure activates complement through the classical pathway," *J. Biol. Chem.* 262(16):7451-7454 (1987).

Kohler, G., et al., "Continuous cultures of fused cells secreting antibody of predefined specificity," *Nature* 256:495-497 (1975).

Kuhlman, M., et al., "The human mannose-binding protein functions as an opsonin," *J. Exp. Med.* 169(5):1733-1745 (1989).

Losman, M.J., et al., "Baboon anti-idiotype antibodies mimic a carcinoembryonic antigen epitope," *Int. J. Cancer* 46(2):310-314 (1990).

Lonberg, N., et al., "Antigen-specific human antibodies from mice comprising four distinct genetic modifications," *Nature* 368:856-859 (1994).

Marks, J.D., et al., "By-passing immunization. Human antibodies from V-gene libraries displayed on phage," *J.Mol.Biol.* 222(3):581-597 (1991).

Matsushita, M., et al., "A novel human serum lectin with collagen- and fibrinogen-like domains that functions as an opsonin," *J. Biol. Chem.* 271(5):2448-2454 (1996).

Mariani, M., et al., "A new enzymatic method to obtain high-yield F(ab)2 suitable for clinical use from mouse IgG1," *Mol. Immunol.* 28(1-2):69-77 (1991).

Morrison, S.L., "Chimeric human antibody molecules: mouse antigen-binding domains with human constant region domains," *Proc. Natl. Acad. Sci. U.S.A.* 81(21):6851-6855 (1984).

Nisonoff, A., et al., "Separation of univalent fragments from the bivalent rabbit antibody molecule by reduction of disulfide bonds," *Arch. Biochem. Biophys.* 89:230-244 (1960).

Zou, Y.R., et al., "Cre-loxP-mediated gene replacement: a mouse strain producing humanized antibodies," *Curr. Biol.* 4(12):1099-1103 (1994).

Whitlow, M., et al., "Single-chain Fv Proteins and Their Fusion Proteins," *Methods: A Companion to Methods in Enzymology* 2:97-105 (1991).

Jones, P.T., et al., "Replacing the complementarity-determining regions in a human antibody with those from a mouse," *Nature* 321:522-525 (1986).

Kelley, R.F. "Engineering Therapeutic Antibodies." *Protein Engineering: Principles and Practice.* Eds. Cleland et al., John Wiley & Sons, Inc.:1996. pp. 399-434.

Iwaki, D., et al., "Production and purification of recombinants of mouse MASP-2 and sMAP," *J Endotoxin. Res.* 11(1):47-50 (2005).

Takahashi, A., et al., "Role of MASP-1 and/or MASP-3 in Activation of the Lectin Pathway," *Int. Immunol.* 2:1220 (2002).

Casavona, J.L., et al., "Human Mannose-binding Lectin in Immunity: Friend, Foe, or Both?" *J. Exp. Med.* 199(10):1295-1299 (2004).

De Vries, B., et al., "The mannose-binding lectin-pathway is involved in complement activation in the course of renal ischemia-reperfusion injury," *Am. J. Pathol.* 165(5):1677-1688 (2004).

BC013893, Strausberg, R.L. et al., "Mus Musculus Mannan-Binding Lectin Serine Peptidase 2, mRNA," *National Center of Biotechnology Information (NCBI) Nucleotide Database* [online], created on Jul. 15, 2006,<http://www.ncbi.nlm.nih.gov/entrez/viewer. fcgi?db=nucleotide&val=1530224> [retrieved Oct. 8, 2014].

Stover, C.M., et al., "Murine serine proteases MASP-1 and MASP-3, components of the lectin pathway activation complex of complement, are encoded by a single structural gene," *Gene Immun.* 4(5):374-384 (2003).

Zou, Y.R., et al., "Generation of a mouse strain that produces immunoglobulin kappa chains with human constant regions," *Science* 262(5137):1271-1274 (1993).

Gerlai, R., "Gene-targeting studies of mammalian behavior: is it the mutation or the background genotype?" *Trends in Neuroscience* 19(5): 177-181 (1996).

Holschneider, D.P., et al., "Genotype to phenotype: challenges and opportunities," *Int. J. Dev. Neurosci.* 18(6):615-618 (2000).

Larivierem W.R., et al., "Transgenic studies of pain and analgesia: mutation or background genotype?" *J. Pharmacol. Exp. Ther.* 297(2):467-473 (2001).

Reichmann, L., et al., "Reshaping human antibodies for therapy," *Nature* 332:323-327 (1988).

Zou, X., et al., "Subtle differences in antibody responses and hypermutation of lambda light chains in mice with a disrupted chi constant region," *Eur. J. Immunol.* 25(8):2154-2162 (1995).

Sauer, B., "Manipulation of transgenes by site-specific recombination: use of Cre recombinase," *Methods Enzymol.* 225:890-900 (1993).

\* cited by examiner

Human MASP-2 specific minigene construct

Human Map19-specific minigene construct

FIG.10A

MASP-2 minigene construct DNA sequence

```
ccggacgtgg tggcgcatgc ctgtaatccc agctactcgg gaggctgagg caggagaatt       60
gctcgaaccc cggaggcaga ggtttggtgg ctcacacctg taatcccagc actttgcgag      120
gctgaggcag gtgcatcgct ttggctcagg agttcaagac cagcctgggc aacacaggga      180
gacccccatc tctacaaaaa acaaaaacaa atataaaggg gataaaaaaa aaaaaaagac      240
aagacatgaa tccatgagga cagagtgtgg aagaggaagc agcagcctca aagttctgga      300
agctggaaga acagataaac aggtgtgaaa taactgcctg gaaagcaact tcttttttt      360
tttttttttt tttgaggtgg agtctcactc tgtcgtccag gctggagtgc agtggtgcga      420
tctcggatca ctgcaacctc cgcctcccag gctcaagcaa ttctcctgcc tcagcctccc      480
gagtagctgg gattataagt gcgcgctgcc acacctggat gatttttgta tttttagtag      540
agatgggatt tcaccatgtt ggtcaggctg gtctcaaact cccaacctcg tgatccaccc      600
accttggcct cccaaagtgc tgggattaca ggtataagcc accgagccca gccaaaagcg      660
acttctaagc ctgcaaggga atcgggaatt ggtggcacca ggtccttctg acagggttta      720
agaaattagc cagcctgagg ctgggcacgg tggctcacac ctgtaatccc agcactttgg      780
gaggctaagg caggtggatc acctgagggc aggagttcaa gaccagcctg accaacatgg      840
agaaacccca tccctaccaa aaataaaaaa ttagccaggt gtggtggtgc tcgcctgtaa      900
tcccagctac ttgggaggct gaggtgggag gattgcttga acacaggaag tagaggctgc      960
agtgagctat gattgcagca ctgcactgaa gccggggcaa cagaacaaga tccaaaaaaa     1020
agggaggggt gaggggcaga gccaggattt gtttccaggc tgttgttacc taggtccgac     1080
tcctggctcc cagagcagcc tgtcctgcct gcctggaact ctgagcaggc tggagtcatg     1140
gagtcgattc ccagaatccc agagtcaggg aggctggggg caggggcagg tcactggaca     1200
aacagatcaa aggtgagacc agcgtagggc tgcagaccag gccaggccag ctggacgggc     1260
acaccatgag gtaggtgggc gcccacagcc tccctgcagg gtgtggggtg ggagcacagg     1320
cctgggccct caccgcccct gccctgccca taggctgctg accctcctgg gccttctgtg     1380
tggctcggtg gccaccccct tgggcccgaa gtggcctgaa cctgtgttcg ggcgcctggc     1440
atcccccggc tttccagggg agtatgccaa tgaccaggag cggcgctgga ccctgactgc     1500
acccccggc taccgcctgc gcctctactt cacccacttc gacctggagc tctcccacct     1560
ctgcgagtac gacttcgtca aggtgccgtc aggacgggag ggctggggtt tctcagggtc     1620
gggggggtccc caaggagtag ccagggttca gggacacctg ggagcagggg ccaggcttgg     1680
ccaggaggga gatcaggcct gggtcttgcc ttcactccct gtgacacctg acccacagc     1740
tgagctcggg ggccaaggtg ctggccacgc tgtgcgggca ggagagcaca gacacggagc     1800
gggcccctgg caaggacact ttctactcgc tgggctccag cctggacatt accttccgct     1860
ccgactactc caacgagaag ccgttcacgg ggttcgaggc cttctatgca gccgagggtg     1920
agccaagagg ggtcctgcaa catctcagtc tgcgcagctg gctgtggggg taactctgtc     1980
ttaggccagg cagccctgcc ttcagtttcc ccacctttcc cagggcaggg gagaggcctc     2040
tggcctgaca tcatccacaa tgcaaagacc aaaacagccg tgacctccat tcacatgggc     2100
tgagtgccaa ctctgagcca gggatctgag gacagcatcg cctcaagtga cgcagggact     2160
ggccgggcgc agcagctcac gcctgtaatt ccagcacttt gggaggccga ggctggctga     2220
tcatttgagg tcaggagttc aaggccagcc agggcaacac ggtgaaactc tatctccact     2280
aaaactacaa aaattagctg ggcgtggtgg tgcgcacctg aatcccagc tactagggag     2340
gctgaggcag gagaattgct tgaacctgcg aggtggaggc tgcagtgaac agagattgca     2400
ccactacact ccagcctggg cgacagagct agactccgtc tcaaaaaca aaaacaaaa     2460
acgacgcagg ggccgagggc cccatttaca gctgacaaag tggggccctg ccagcgggag     2520
cgctgccagg atgtttgatt tcagatccca gtccctgcag agaccaactg tgtgacctct     2580
ggcaagtggc tcaatttctc tgctccttag gaagctgctg caagggttca gcgctgtagc     2640
cccgccccct gggtttgatt gactcccctc attagctggg tgacctcggg ccggacactg     2700
aaactcccac tggtttaaca gaggtgatgt ttgcatcttt ctcccagcgc tgctgggagc     2760
ttgcagcgac cctaggcctg taaggtgatt ggcccggcac cagtcccgca cctagacag     2820
gacgaggcct cctctgaggt ccactctgag gtcatggatc tcctgggagg agtccaggct     2880
ggatcccgcc tctttccctc ctgacggcct gcctggccct gcctctcccc cagacattga     2940
cgagtgccag gtggccc                                                    2957
```

FIG.10B

The human genomic sequence of the *MASP2* gene (above) is fused to the 5' end
of our MASP-2 cDNA (below) using a Xma I site (CC/CGGG)

```
................................CGGGAGAGGCGCCCACCTGCGACCACCACTGCCACAACCACCTGGGCGGTTTC      525
TACTGCTCCTGCCGCGCAGGCTACGTCCTGCACCGTAACAAGCGCACCTGCTCAGCCCTGTGCTCCGGCCAGGTC      600
TTCACCCAGAGGTCTGGGGAGCTCAGCAGCCCTGAATACCCACGGCCGTATCCCAAACTCTCCAGTTGCACTTAC      675
AGCATCAGCCTGGAGGAGGGGTTCAGTGTCATTCTGGACTTTGTGGAGTCCTTCGATGTGGAGACACACCCTGAA      750
ACCCTGTGTCCCTACGACTTTCTCAAGATTCAAACAGACAGAGAAGAACATGGCCCATTCTGTGGGAAGACATTG      825
CCCCACAGGATTGAAACAAAAAGCAACACGGTGACCATCACCTTTGTCACAGATGAATCAGGAGACCACACAGGC      900
TGGAAGATCCACTACACGAGCACAGCGCACGCTTGCCCTTATCCGATGGCGCCACCTAATGGCCACGTTTCACCT      975
GTGCAAGCCAAATACATCCTGAAAGACAGCTTCTCCATCTTTTGCGAGACTGGCTATGAGCTTCTGCAAGGTCAC     1050
TTGCCCCTGAAATCCTTTACTGCAGTTTGTCAGAAAGATGGATCTTGGGACCGGCCAATGCCCGCGTGCAGCATT     1125
GTTGACTGTGGCCCTCCTGATGATCTACCCAGTGGCCGAGTGGAGTCACATCACAGGTCCTGGAGTGACCACCTAC     1200
AAAGCTGTGATTCAGTACAGCTGTGAAGAGACCTTCTACACAATGAAAGTGAATGATGGTAAATATGTGTGTGAG     1275
GCTGATGGATTCTGGACGAGCTCCAAAGGAGAAAAATCACTCCCAGTCTGTGAGCCTGTTTGTGGACTATCAGCC     1350
CGCACAACAGGAGGGCGTATATATGGAGGGCAAAAGGCAAAACCTGGTGATTTTCCTTGGCAAGTCCTGATATTA     1425
GGTGGAACCACAGCAGCAGGTGCACTTTTATATGACAACTGGGTCCTAACAGCTGCTCATGCCGTCTATGAGCAA     1500
AAACATGATGCATCCGCCCTGGACATTCGAATGGGCACCCTGAAAAGACTATCACCTCATTATACACAAGCCTGG     1575
TCTGAAGCTGTTTTTATACATGAAGGTTATACTCATGATGCTGGCTTTGACAATGACATAGCACTGATTAAATTG     1650
AATAACAAAGTTGTAATCAATAGCAACATCACGCCTATTTGTCTGCCAAGAAAAGAAGCTGAATCCTTTATGAGG     1725
ACAGATGACATTGGAACTGCATCTGGATGGGGATTAACCCAAAGGGGTTTTCTTGCTAGAAATCTAATGTATGTC     1800
GACATACCGATTGTTGACCATCAAAAATGTACTGCTGCATATGAAAAGCCACCCTATCCAAGGGGAAGTGTAACT     1875
GCTAACATGCTTTGTGCTGGCTTAGAAAGTGGGGGCAAGGACAGCTGCAGAGGTGACAGCGGAGGGGCACTGGTG     1950
TTTCTAGATAGTGAAACAGAGAGGTGGTTTGTGGGAGGAATAGTGTCCTGGGGTTCCATGAATTGTGGGGAAGCA     2025
GGTCAGTATGGAGTCTACACAAAAGTTATTAACTATATTCCCTGGATCGAGAACATAATTAGTGATTTTTAActt     2100
gcgtgtctgcagtcaaggattcttcatttttagaaatgcctgtgaagaccttggcagcgacgtggctcgagaagc     2175
attcatcattactgtggacatggcagttgttgctccacccaaaaaaacagactccaggtgaggctgctgtcattt     2250
ctccacttgccagtttaattccagccttacccattgactcaaggggacataaaccacgagagtgacagtcatctt     2325
tgcccacccagtgtaatgtcactgctcaaattacatttcattaccttaaaaagccagtctcttttcatactggct     2400
gttggcatttctgtaaactgcctgtccatgctctttgttttaaacttgttcttattgaaaaaaaaaaaaaaaa      2475
```

FIG.11A

Map19 minigene construct DNA sequence

```
ccggacgtgg tggcgcatgc ctgtaatccc agctactcgg gaggctgagg caggagaatt    60
gctcgaaccc cggaggcaga ggtttggtgg ctcacacctg taatcccagc actttgcgag   120
gctgaggcag gtgcatcgct ttggctcagg agttcaagac cagcctgggc aacacaggga   180
gaccccatc tctacaaaaa acaaaaacaa atataaaggg gataaaaaaa aaaaaaagac    240
aagacatgaa tccatgagga cagagtgtgg aagaggaagc agcagcctca aagttctgga   300
agctggaaga acagataaac aggtgtgaaa taactgcctg gaaagcaact tcttttttt    360
tttttttttt tttgaggtgg agtctcactc tgtcgtccag gctggagtgc agtggtgcga   420
tctcggatca ctgcaacctc cgcctccag gctcaagcaa ttctcctgcc tcagcctccc    480
gagtagctgg gattataagt gcgcgctgcc acacctggat gatttttgta ttttagtag    540
agatgggatt tcaccatgtt ggtcaggctg gtctcaaact cccaacctcg tgatccaccc   600
accttggcct cccaaagtgc tgggattaca ggtataagcc accgagccca gccaaaagcg   660
acttctaagc ctgcaaggga atcgggaatt ggtggcacca ggtccttctg acagggttta   720
agaaattagc cagcctgagg ctgggcacgg tggctcacac ctgtaatccc agcactttgg   780
gaggctaagg caggtggatc acctgagggc aggagttcaa gaccagcctg accaacatgg   840
agaaacccca tccctaccaa aaataaaaaa ttagccaggt gtggtggtgc tcgcctgtaa   900
tcccagctac ttgggaggct gaggtgggag gattgcttga acacaggaag tagaggctgc   960
agtgagctat gattgcagca ctgcactgaa gccggggcaa cagaacaaga tccaaaaaaa  1020
agggaggggt gaggggcaga gccaggattt gtttccaggc tgttgttacc taggtccgac  1080
tcctggctcc cagagcagcc tgtcctgcct gcctggaact ctgagcaggc tggagtcatg  1140
gagtcgattc ccagaatccc agagtcaggg aggctggggg caggggcagg tcactggaca  1200
aacagatcaa aggtgagacc agcgtagggc tgcagaccag gccaggccag ctggacgggc  1260
acaccatgag gtaggtgggc gcccacagcc tccctgcagg gtgtggggtg ggagcacagg  1320
cctgggccct caccgcccct gccctgccca taggctgctg accctcctgg gccttctgtg  1380
tggctcggtg gccacccct tgggcccgaa gtggcctgaa cctgtgttcg ggcgcctggc   1440
atccccggc tttccagggg agtatgccaa tgaccaggag cggcgctgga ccctgactgc   1500
accccccggc taccgcctgc gcctctactt cacccacttc gacctggagc tctcccacct   1560
ctgcgagtac gacttcgtca aggtgccgtc aggacgggag ggctggggtt tctcagggtc   1620
gggggggtccc caaggagtag ccagggttca gggacacctg ggagcagggg ccaggcttgg  1680
ccaggaggga gatcaggcct gggtcttgcc ttcactccct gtgacacctg accccacagc  1740
tgagctcggg ggccaaggtg ctggccacgc tgtgcgggca ggagagcaca gacacggagc  1800
gggcccctgg caaggacact ttctactcgc tgggctccag cctggacatt accttccgct  1860
ccgactactc caacgagaag ccgttcacgg ggttcgaggc cttctatgca gccgagggtg  1920
agccaagagg ggtcctgcaa catctcagtc tgcgcagctg gctgtggggg taactctgtc  1980
ttaggccagg cagccctgcc ttcagtttcc ccacctttcc cagggcaggg gagaggcctc  2040
tggcctgaca tcatccacaa tgcaaagacc aaaacagccg tgacctccat tcacatgggc  2100
tgagtgccaa ctctgagcca gggatctgag gacagcatcg cctcaagtga cgcagggact  2160
ggccgggcgc agcagctcac gcctgtaatt ccagcacttt ggggaggcga ggctggctga  2220
tcatttgagg tcaggagttc aaggccagcc agggcaacac ggtgaaactc tatctccact  2280
aaaactacaa aaattagctg ggcgtggtgg tgcgcacctg aatcccagc tactagggag   2340
gctgaggcag gagaattgct tgaacctgcg aggtggaggc tgcagtgaac agagattgca  2400
ccactacact ccagcctggg cgacagagct agactccgtc tcaaaaaaca aaaacaaaa   2460
acgacgcagg ggccgagggc cccatttaca gctgacaaag tggggccctg ccagcgggag  2520
cgctgccagg atgtttgatt tcagatccca gtccctgcag agaccaactg tgtgacctct  2580
ggcaagtggc tcaatttctc tgctccttag gaagctgctg caagggttca gcgctgtagc  2640
cccgccccct gggtttgatt gactcccctc attagctggg tgacctcggg ccggacactg  2700
aaactcccac tggtttaaca gaggtgatgt ttgcatcttt ctcccagcgc tgctgggagc  2760
ttgcagcgac cctaggcctg taaggtgatt ggcccggcac cagtcccgca ccctagacag  2820
gacgaggcct cctctgaggt ccactctgag gtcatggatc tcctgggagg agtccaggct  2880
ggatcccgcc tctttccctc ctgacggcct gcctggccct gcctctcccc cagacattga  2940
cgagtgccag gtggccc                                                  2957
```

FIG.11B

The human genomic sequence of the *MASP2* gene (above) is fused to the 5' end of our MAp19 cDNA (below) using a Xma I site (CC/CGGG)

```
              100                          110                          120
........................CGGGAGAGGCGCCCACCTGCGACCACCACTGCCACAACCACCTGGGCGGTTTC
  I   D   E   C   Q   V   A   P   G   E   A   P   T   C   D   H   H   C   H   N   H   L   G   G   F
                      130                                  140
TACTGCTCCTGCCGCGCAGGCTACGTCCTGCACCGTAACAAGCGCACCTGCTCAGAGCAGAGCCTCTAGcctccc
  Y   C   S   C   R   A   G   Y   V   L   H   R   N   K   R   T   C   S   E   Q   S   L  stop
      150´                                160                          170
ctggagctccggctgcccagcaggtcagaagccagagccagcctgctggcctcagctccggggttgggctgagatg ctgtgccccaactcccattcacccaccatggacccaataataaacctggccccacccaaaaaaaaaaaaaaaaaa
```

GENETICALLY MODIFIED NON-HUMAN MAMMALS AND CELLS

FIELD OF THE INVENTION

The present invention relates to genetically modified non-human mammals, in particular to genetically modified rodents such as mice, which do not produce any endogenous mannan-binding lectin associated serine protease 2 (MASP-2) polypeptide. The invention also relates to genetically modified non-human cells, particularly embryonic stem cells, especially rodent cells such as mouse cells, which do not produce any endogenous MASP-2 polypeptide. The invention also relates to genetically modified non-human cells, particularly embryonic stem cells and genetically modified non-human mammals produced therefrom, and their use in the production of non-human mammals and cells from which the endogenous MASP-2 genes have been deleted from or disrupted within the genome. Aspects of the invention also relate to genetically modified non-human mammals and cells which do not produce any endogenous mannan binding lectin associated protein 19 (MAp 19) protein.

CROSS REFERENCE TO RELATED APPLICATIONS

This application is a continuation of U.S. patent application Ser. No. 14/316,235, filed Jun. 26, 2014, now abandoned, which is a divisional of U.S. patent application Ser. No. 11/570,087, filed Feb. 12, 2009, now issued as U.S. Pat. No. 8,785,717, which is a 371 National Phase Application of International PCT Application No. PCT/GB2005/050086, filed Jun. 8, 2005, now lapsed, which claims benefit of Great Britain Patent Application No. GB 0412966.40, filed Jun. 10, 2004, now lapsed.

STATEMENT REGARDING SEQUENCE LISTING

The sequence listing associated with this application is provided in text format in lieu of a paper copy and is hereby incorporated by reference into the specification. The name of the text file containing the sequence listing is MP_1_0046_US4_Sequence_Listing_as_Filed_20161109.txt. The text file is 11 KB, was created on Nov. 9, 2016; and is being submitted via EFS-Web with the filing of the specification.

BACKGROUND OF THE INVENTION

The complement system provides an early acting mechanism to initiate and amplify the inflammatory response to microbial infection and other acute insults (Liszewski, M. K. and J. P. Atkinson, 1993, in Fundamental Immunology, Third Edition, edited by W. E. Paul, Raven Press, Ltd., New York). While complement activation provides a valuable first-line defence against potential pathogens, the activities of complement that promote a protective inflammatory response can also represent a potential threat to the host (Kalli, K. R., et al., Springer Semin. Immunopathol. 15:417-431, 1994; Morgan, B. P., Eur. J. Clinical Investig. 24:219-228, 1994). For example, C3 and C5 proteolytic products recruit and activate neutrophils. These activated cells are indiscriminate in their release of destructive enzymes and may cause organ damage. In addition, complement activation may cause the deposition of lytic complement components on nearby host cells as well as on microbial targets, resulting in host cell lysis.

The complement system has been implicated as contributing to the pathogenesis of numerous acute and chronic disease states, including; myocardial infarction, revascularization following stroke, ARDS, reperfusion injury, septic shock, capillary leakage following thermal burns, post-cardiopulmonary bypass inflammation, transplant rejection, rheumatoid arthritis, multiple sclerosis, myasthenia gravis, and Alzheimer's disease. In almost all of these conditions, complement is not the cause but is one of several factors involved in pathogenesis. Nevertheless, complement activation may be a major pathological mechanism and represents an effective point for clinical control in many of these disease states. The growing recognition of the importance of complement-mediated tissue injury in a variety of disease states underscores the need for effective complement inhibitory drugs. No drugs have been approved for human use that specifically target and inhibit complement activation.

Currently, it is widely accepted that the complement system can be activated through three distinct pathways: the classical pathway, the lectin pathway, and the alternative pathway. The classical pathway is usually triggered by antibody bound to a foreign particle (i.e., an antigen) and thus requires prior exposure to that antigen for the generation of specific antibody. Since activation of the classical pathway is associated with development of an immune response, the classical pathway is part of the acquired immune system. In contrast, both the lectin and alternative pathways are independent of clonal immunity and are part of the innate immune system.

The first step in activation of the classical pathway is the binding of a specific recognition molecule, C1q, to antigen-bound IgG and IgM. The activation of the complement system results in the sequential activation of serine protease zymogens. C1q is associated with the C1r and C1s serine protease proenzymes as a complex called C1 and, upon binding of C1q to an immune complex, autoproteolytic cleavage of the Arg-Ile site of C1r is followed by C1r activation of C1s, which thereby acquires the ability to cleave C4 and C2. The cleavage of C4 into two fragments, designated C4a and C4b, allows the C4b fragments to form covalent bonds with adjacent hydroxyl or amino groups and the subsequent generation of C3 convertase (C4b2b) through noncovalent interaction with the C2b fragment of activated C2. C3 convertase (C4b2b) activates C3 leading to generation of the C5 convertase (C4b2b3b) and formation of the membrane attack complex (C5b-9) that can cause microbial lysis. The activated forms of C3 and C4 (C3b and C4b) are covalently deposited on the foreign target surfaces, which are recognized by complement receptors on multiple phagocytes.

Independently, the first step in activation of the complement system by the lectin pathway is also the binding of specific recognition molecules, which is followed by the activation of associated serine proteases. However, rather than the binding of immune complexes by C1q, the recognition molecules in the lectin pathway are serum carbohydrate-binding proteins (mannan-binding lectin (MBL), H-ficolin, M-ficolin, and L-ficolin) (Lu, J., et al., Biochim. Biophys. Acta 1572:387-400, 2002). Ikeda et al. first demonstrated that, like C1q, MBL could activate the complement system upon binding to yeast mannan-coated erythrocytes in a C4-dependent manner (Ikeda, K., et al., J. Biol. Chem. 262:7451-7454, 1987). MBL, a member of the collectin protein family, is a calcium-dependent lectin that binds carbohydrates with 3- and 4 hydroxy groups oriented in the equatorial plane of the pyranose ring. Prominent ligands for MBL are thus D-mannose and N acetyl-D-glucosamine, while carbohydrates not fitting this steric requirement have undetectable affinity for MBL (Weis, W. I., et al., Nature 360:127-134, 1992). The interaction between MBL and monovalent sugars is extremely weak, with dissociation constants typically in the 2 mM range. MBL achieves tight, specific binding to glycan ligands by interaction with multiple monosaccharide residues simultaneously (Lee, R. T., et al., Archiv. Biochem. Biophys. 299: 129-136, 1992). MBL recognizes the carbohydrate patterns that commonly decorate micro organisms such as bacteria, yeast, parasites and certain viruses. In contrast, MBL does not recognize D-galactose and sialic acid, the penultimate and ultimate sugars that usually decorate 'mature' complex glycoconjugates present on mammalian plasma and cell surface glycoproteins. This binding specificity is thought to help protect from self activation. However, MBL does bind with high affinity to clusters of high-mannose 'precursor' glycans on N-linked glycoproteins and glycolipids sequestered in the endoplasmic reticulum and Golgi of mammalian cells (Maynard, Y., et al., J. Biol. Chem. 257:3788-3794, 1982). Therefore, damaged cells are potential targets for lectin pathway activation via MBL binding.

The ficolins possess a different type of lectin domain than MBL, called the fibrinogen like domain. Ficolins bind sugar residues in a Ca++-independent manner. In humans, three kinds of ficolins, L-ficolin, M-ficolin and H-ficolin, have been identified. Both serum ficolins L-ficolin and H-ficolin have in common a specificity for N-acetyl-D-glucosamine; however, H ficolin also binds N-acetyl-D-galactosamine. The difference in sugar specificity of L ficolin, H ficolin and MBL means that the different lectins may be complementary and target different, though overlapping, glycoconjugates. This concept is supported by the recent report that, of the known lectins in the lectin pathway, only L-ficolin binds specifically to lipoteichoic acid, a cell wall glycoconjugate found on all Gram-positive bacteria (Lynch, N. J., et al., J. Immunol 172:1198-1202, 2004). The collectins (i.e., MBL) and the ficolins bear no significant similarity in amino acid sequence. However, the two groups of proteins have similar domain organizations and, like C1q, assemble into oligomeric structures, which maximize the possibility of multisite binding. The serum concentrations of MBL are highly variable in healthy populations and this is genetically controlled by the polymorphism/mutations in both the promoter and coding regions of the MBL gene. As an acute phase protein, the expression of MBL is further upregulated during inflammation. L ficolin is present in serum at similar concentrations as MBL. Therefore, the L ficolin arm of the lectin pathway is potentially comparable to the MBL arm in strength. MBL and ficolins can also function as opsonins, which require interaction of these proteins with phagocyte receptors (Kuhlman, M., et al., J. Exp Med. 169:1733, 1989; Matsushita, M., et al., J. Biol. Chem. 271:2448-54, 1996). However, the identities of the receptor(s) on phagocytic cells have not been established.

Human MBL forms a specific and high affinity interaction through its collagen-like domain with unique C1r/C1s-like serine proteases, termed MBL-associated serine proteases (MASPs). To date, three MASPs have been described. First, a single enzyme "MASP" was identified and characterized as the enzyme responsible for the initiation of the complement cascade (i.e., cleaving C2 and C4) (Ji, Y. H., et al., J. Immunol. 150:571-578, 1993). Later, it turned out that MASP is in fact a mixture of two proteases: MASP-1 and MASP-2 (Thiel, S., et al., Nature 386:506-510, 1997). However, it was demonstrated that the MBL-MASP-2 complex alone is sufficient for complement activation (Vorup-Jensen, T., et al., J. Immunol. 165:2093-2100, 2000). Furthermore, only MASP-2 cleaved C2 and C4 at high rates (Ambrus, G., et al., J. Immunol. 170:1374-1382, 2003). Therefore, MASP-2 is the protease responsible for activating C4 and C2 to generate the C3 convertase, C4b2a. This is a significant difference from the C1 complex, where the coordinated action of two specific serine proteases (C1r and C1s) leads to the activation of the complement system. Recently, a third novel protease, MASP-3, has been isolated (Dahl, M. R., et al., Immunity 15:127-35, 2001). MASP-1 and MASP-3 are alternatively spliced products of the same gene (Stover et al., Genes and Immunity 4: 374-384 (2003). The biological functions of MASP-1 and MASP-3 remain to be resolved.

MASPs share identical domain organizations with those of C1r and C1s, the enzymatic components of the C1 complex (Sim, R. B., et al., Biochem. Soc. Trans. 28:545, 2000). These domains include an N-terminal C1r/C1s/sea urchin Uegf/bone morphogenic protein (CUB) domain, an epidermal growth factor-like domain, a second CUB domain, a tandem of complement control protein domains, and a serine protease domain. As in the C1 proteases, activation of MASP-2 occurs through cleavage of an Arg-Ile bond adjacent to the serine protease domain, which splits the enzyme into disulfide-linked A and B chains, the latter consisting of the serine protease domain. Recently, a genetically determined deficiency of MASP-2 was described (Stengaard-Pedersen, K., et al., New Eng. J. Med. 349:554-560, 2003). The mutation of a single nucleotide leads to an Asp-Gly exchange in the CUB1 domain and renders MASP-2 incapable of binding to MBL.

MBL is also associated with a nonenzymatic protein referred to as MBL-associated protein of 19 kDa (MAp19) (Stover, C. M., J. Immunol. 162:3481-90, 1999) or small MBL-associated protein (sMAP) (Takahashi, M., et al., Int. Immunol. 11:859-863, 1999). MAp19 is formed by alternative splicing of the MASP 2 gene product and comprises the first two domains of MASP-2, followed by an extra sequence of four unique amino acids. The biological function of MAp19 is unknown. The MASP 1 and MASP 2 genes are located on chromosomes 3 and 1, respectively (Schwaeble, W., et al., Immunobiology 205:455-466, 2002).

Several lines of evidence suggest that there are different MBL-MASPs complexes and a large fraction of the total MASPs in serum is not complexed with MBL (Thiel, S., et al., J. Immunol. 165:878-887, 2000). Both H- and L-ficolin are associated with MASP and activate the lectin complement pathway, as does MBL (Dahl, M. R., et al., Immunity 15:127-35, 2001; Matsushita, M., et al., J. Immunol. 168: 3502-3506, 2002). Both the lectin and classical pathways form a common C3 convertase (C4b2a) and the two pathways converge at this step.

The lectin pathway is widely thought to have a major role in host defence against infection. Strong evidence for the involvement of MBL in host defence comes from analysis of patients with decreased serum levels of functional MBL (Kilpatrick, D. C., Biochim. Biophys. Acta 1572:401-413, 2002). Such patients display susceptibility to recurrent bacterial and fungal infections. These symptoms are usually evident early in life, during an apparent window of vulnerability as maternally derived antibody titer wanes, but before a full repertoire of antibody responses develops. This syndrome often results from mutations at several sites in the collagenous portion of MBL, which interfere with proper formation of MBL oligomers. However, since MBL can function as an opsonin independent of complement, it is not known to what extent the increased susceptibility to infection is due to impaired complement activation.

Although there is extensive evidence implicating both the classical and alternative complement pathways in the pathogenesis of non-infectious human diseases, the role of the lectin pathway is just beginning to be evaluated. Recent studies provide evidence that activation of the lectin pathway can be responsible for complement activation and related inflammation in ischemia/reperfusion injury. Collard et al. (2000) reported that cultured endothelial cells subjected to oxidative stress bind MBL and show deposition of C3 upon exposure to human serum (Collard, C. D., et al., Am. J. Pathol. 156:1549-1556, 2000). In addition, treatment of human sera with blocking anti-MBL monoclonal antibodies inhibited MBL binding and complement activation. These findings were extended to a rat model of myocardial ischemia-reperfusion in which rats treated with a blocking antibody directed against rat MBL showed significantly less myocardial damage upon occlusion of a coronary artery than rats treated with a control antibody (Jordan, J. E., et al., Circulation 104:1413-1418, 2001). The molecular mechanism of MBL binding to the vascular endothelium after oxidative stress is unclear; a recent study suggests that activation of the lectin pathway after oxidative stress may be mediated by MBL binding to vascular endothelial cytokeratins, and not to glycoconjugates (Collard, C. D., et al., Am. J. Pathol. 159:1045-1054, 2001). Other studies have implicated the classical and alternative pathways in the pathogenesis of ischemia/reperfusion injury and the role of the lectin pathway in this disease remains controversial (Riedermann, N.C., et al., Am. J. Pathol. 162:363-367, 2003).

In contrast to the classical and lectin pathways, no initiators of the alternative pathway have been found to fulfil the recognition functions that C1q and lectins perform in the other two pathways. Currently it is widely accepted that the alternative pathway is spontaneously triggered by foreign or other abnormal surfaces (bacteria, yeast, virally infected cells, or damaged tissue). There are four plasma proteins directly involved in the alternative pathway: C3, factors B and D, and properdin. Proteolytic generation of C3b from native C3 is required for the alternative pathway to function. Since the alternative pathway C3 convertase (C3bBb) contains C3b as an essential subunit, the question regarding the origin of the first C3b via the alternative pathway has presented a puzzling problem and has stimulated considerable research.

C3 belongs to a family of proteins (along with C4 and α-2 macroglobulin) that contain a rare post-translational modification known as a thioester bond. The thioester group is composed of a glutamine whose terminal carbonyl group is bound to the sulfhydryl group of a cysteine three amino acids away. This bond is unstable and the electrophilic carbonyl group of glutamine can form a covalent bond with other molecules via hydroxyl or amino groups. The thioester bond is reasonably stable when sequestered within a hydrophobic pocket of intact C3. However, proteolytic cleavage of C3 to C3a and C3b results in exposure of the highly reactive thioester bond on C3b and by this mechanism C3b covalently attaches to a target. In addition to its well-documented role in covalent attachment of C3b to complement targets, the C3 thioester is also thought to have a pivotal role in triggering the alternative pathway. According to the widely accepted "tick-over theory", the alternative pathway is initiated by the generation of a fluid-phase convertase, C3bBb, which is formed from C3 with hydrolyzed thioester (C3b; C3H20) and factor B (Lachmann, P. J., et al., Springer Semin. Immunopathol. 7:143-162, 1984). The C3b-like iC3 is generated from native C3 by a slow spontaneous hydrolysis of the internal thioester in the protein (Pangburn, M. K., et al., J. Exp. Med. 154:856-867, 1981). Through the activity of the C3bBb convertase, C3b molecules are deposited on the target surface thereby initiating the alternative pathway.

Very little is known about the initiators of activation of the alternative pathway. Activators are thought to include yeast cell walls (zymosan), many pure polysaccharides, rabbit erythrocytes, certain immunoglobulins, viruses, fungi, bacteria, animal tumour cells, parasites, and damaged cells. The only feature common to these activators is the presence of carbohydrate, but the complexity and variety of carbohydrate structures has made it difficult to establish the shared molecular determinants, which are recognized.

The alternative pathway can also provide a powerful amplification loop for the lectin/classical pathway C3 convertase (C4b2b) since any C3b generated can participate with factor B in forming additional alternative pathway C3 convertase (C3bBb). The alternative pathway C3 convertase is stabilized by the binding of properdin. Properdin extends the alternative pathway C3 convertase half-life six to ten fold. Addition of C3b to the C3 convertase leads to the formation of the alternative pathway C5 convertase.

All three pathways (i.e., the classical, lectin and alternative) have been thought to converge at C5, which is cleaved to form products with multiple proinflammatory effects. The converged pathway has been referred to as the terminal complement pathway. C5a is the most potent anaphylatoxin, inducing alterations in smooth muscle and vascular tone, as well as vascular permeability. It is also a powerful chemotaxin and activator of both neutrophils and monocytes. C5a-mediated cellular activation can significantly amplify inflammatory responses by inducing the release of multiple additional inflammatory mediators, including cytokines, hydrolytic enzymes, arachidonic acid metabolites and reactive oxygen species. C5 cleavage leads to the formation of C5b-9, also known as the membrane attack complex (MAC). There is now strong evidence that sublytic MAC deposition may play an important role in inflammation in addition to its role as a lytic pore-forming complex.

SUMMARY OF THE INVENTION

We have now created a knockout organism with a targeted disruption of the MASP-2 gene, and which is deficient in the lectin complement pathway. Such organisms are useful as a model to study the role of lectin pathway deficiency in health and disease. The organisms are potentially useful as experimental models for disorders such as reperfusion injury, myocardial infarction, stroke, and transplantation. The organisms may also be useful for the production of antibodies against human MASP-2 for use as a therapeutic tool. We have also produced organisms which are deficient in the production of MAp 19.

Accordingly the present invention provides a genetically modified non-human mammal or a genetically modified non-human mammalian cell characterised in that it does not comprise a nucleic acid sequence which itself encodes an endogenous MASP-2 polypeptide. The invention also provides a genetically modified or transgenic mouse wherein the germ cells contain a disrupted MASP-2 gene. The invention further provides a genetically modified transgenic mouse or the progeny thereof, wherein the somatic and germ cells are free from endogenous MASP-2.

In an aspect of the invention, the genetically modified non-human mammal or cell does not comprise a nucleic acid sequence which itself encodes an MASP-2 polypeptide.

Herein, endogenous is defined as authentic, native, not foreign and not modified by genetic engineering such as gene targeting or gene introduction.

Genetically modified non-human mammals or cells are obtainable by targeted deletion of all or essentially all endogenous MASP-2 gene sequences. The deletion can be of all endogenous MASP-2 genes and intervening sequences (complete exon/intron removal or clean deletion) or essentially all endogenous MASP-2 sequences by deletion of an extensive part of the endogenous MASP-2 gene sequence such that expression of the MASP-2 gene is prevented. Targeted deletion can be performed by a homologous recombination process, or by a recombination-excision process, for example by Cre-loxP recombination. Thus the invention further provides a genetically modified or transgenic non-human mammal as described herein or a genetically modified or transgenic non-human mammalian cell, preferably an embryonic stem cell as described herein, obtainable by a homologous recombination method.

The Cre-loxP recombination system is described in Zou et al (Science, 1993; 262, 1271-1274). This describes a system that operates in mammalian cells and has been used for gene targeting experiments in the mouse to generate "clean" deletions of target genes in the germ line, as well as to inactivate genes in a conditional manner (based on regulated expression of Cre recombinase).

Cre is a 38 kDa recombinase protein from bacteriophage P1 which mediates intramolecular (excisive or inversional) and intermolecular (integrative) site specific recombination between loxP sites; for a review of the system refer to Sauer in Methods of Enzymology; 1993, Vol. 225, 890-900. A loxP site (the locus of crossing over) consists of two 13 bp inverted repeats separated by an 8 bp asymmetric spacer region. One molecule of Cre binds per inverted repeat, or two Cre molecules line up at one loxP site. The recombination occurs in the asymmetric spacer region. Those 8 bases are also responsible for the directionality of the site. Two loxP sequences in opposite orientation to each other invert the intervening piece of DNA, two sites in direct orientation dictate excision of the intervening DNA between the sites, leaving one loxP site behind. This precise removal of DNA can be used to eliminate genes (gene deletion) or to activate genes. The Cre-loxP system can also be used to introduce genes (gene introduction). A gene flanked by two loxP sites in a direct orientation is referred to as a "floxed gene".

Zou et al (Current Biology 1994; 4: (12) 1099-2003) describe use of the Cre-loxP system in mouse embryonic stem cells to replace the mouse gene Cg1, which encodes the constant region of the heavy chain of IgG1 antibodies, with the corresponding human gene Cg1. A targeting construct was generated in which a loxP site was cloned at the 3'end of the target gene sequence (in this instance the mouse Cg1) and, at a position 5' of the target gene, an insertion was made of (from 5' to 3') a mutant gene of interest (in this instance human Cg1), a loxP site, a negative selection marker (HSV-tk) and a positive selection marker (neor). In the construct the loxP sites were in direct orientation. The targeting construct was introduced by transfection into ES cells, transformants were selected on G418 by neomycin resistance. A Cre construct was introduced into the transformed cells to achieve transient expression of Cre. Recombination, that is excision of the sequence between the two loxP sites (encoding HSV-tk, neor and the endogenous target gene mouse Cg1), occurred only in those cells expressing Cre recombinase. The human Cg1 sequence was situated outside the loxP sites and thus remained inserted within the mouse genome. Negative selection using acyclovir or gancyclovir was used to identify those cells in which the deletion had taken place, as only cells that do not express HSV-tk, i.e. those in which the endogenous mouse Cg1 gene has also been deleted, were able to survive on those media.

Thus, Zou et al (1994) used the Cre-loxP system to introduce a human Cg1 gene and then delete a single endogenous Ig heavy chain constant region gene, Cg1. The exons encoding the transmembrane and cytoplasmic portions of the IgH mouse Cg1 were not replaced by human sequences, these were retained to minimise the risk of disturbing membrane expression and signalling of the humanised IgG1 in the mouse. The introduced human Cg1 gene was transmitted through the mouse germline and the resulting mutant mice were crossed with mice expressing kappa light chains with a human, instead of mouse constant region. Mice homozygous for both insertions produce humanised kappa chain bearing IgG1 antibodies.

In site specific recombination methods for targeted deletion, a region of nucleic acid sequence flanked by two site specific recombination sequences is excised; the excised region may be replaced with exogenous sequences; for example, selectable markers to identify recombinants, or replacement genes.

A genetically modified non-human mammal or cell of the invention may comprise one or more selectable marker(s) integrated within the genome.

The selectable marker is preferably one or more of: a neomycin resistance gene; a puromycin resistance gene; a hygromycin gene or a herpes simplex virus thymidine kinase gene. Two or more selectable markers may be used.

Thus the invention also provides a non-human mammal or non-human mammalian cell, preferably a rodent cell, more preferably a mouse cell, most preferably a mouse embryonic stem cell, free from endogenous MASP-2 peptide and comprising one or more gene(s) encoding a selectable marker.

A genetically modified non-human mammal of the invention can be rodent, murine, ovine, porcine, equine, canine, feline or the like, but is preferably a rodent, more preferably murine, most preferably a mouse. A genetically modified non-human mammalian cell of the invention may be an embryonic stem cell or an oocyte; and is preferably a rodent, murine, ovine, porcine, equine, canine or feline cell, or the like, preferably a rodent cell, more preferably a murine cell, most preferably a mouse cell. Mice are particularly preferred as they are easy to handle and breed.

The present invention provides a mouse in which the endogenous MASP-2 gene is absent, or partially absent to the extent that the gene is non-functional. By partially absent it is meant that the endogenous MASP-2 gene sequence has been deleted or disrupted to the extent that no functional endogenous MASP-2 gene product is encoded at the MASP-2 locus, i.e. that no functional endogenous MASP-2 gene product could be expressed from the locus.

The present invention further provides a non-human mammalian embryonic stem (ES) cell characterised in that the endogenous MASP-2 gene is absent or partially absent.

The genetically modified non-human mammal, preferably a rodent, more preferably a mouse, can be bred with a compatible non-human mammal that is able to express one or more functionally active MASP-2 genes, preferably one or more functionally active human MASP-2 genes, e.g. a deletion mutant mouse can be bred with a mouse capable of expressing one or more functionally active human MASP-2 genes. The heterozygous progeny (F1) of this cross can be inter-bred to produce heterozygous and homozygous progeny (F2) of a non-human mammal, preferably a mouse, that is not able to express the endogenous MASP-2 gene and instead is able to express only a foreign, preferably human, MASP-2 gene.

The invention provides a genetically modified non-human mammal derived from a genetically modified non-human mammal as described herein, or from a genetically modified non-human cell as described herein, and provides a genetically modified non-human cell derived from a genetically modified non-human mammal as described herein.

The invention provides a method for producing a genetically modified non-human cell comprising: transfecting a non-human cell with a targeting construct for integration in place of the endogenous MASP-2 gene, said targeting construct comprising a targeting recombination sequence and a selectable marker; and selecting for a cell in which the selectable marker is present.

It is preferred that the genetically modified non-human cell is an embryonic stem cell or an oocyte. The genetically modified non-human cell can be a rodent cell, more preferably a mouse cell.

Any suitable cloning vector may be used to generate the targeting construct, cloning strategies are described by Sambrook, Fritsch and Maniatis in Molecular Cloning, A Laboratory Manual, Cold Spring Harbor Laboratory Press, 1989. Desirably, the targeting construct may carry one or more marker genes; suitable markers are known, especially suitable are those that allow for positive selection. Of particular interest is the use of the gene for neomycin phosphotransferase ("neo"), which confers resistance to G418, also suitable is the puromycin resistance gene ("puro") or the hygromycin resistance gene; neomycin and/or puromycin resistance genes are preferred.

In the targeting construct, upstream and/or downstream from the target gene, may be a gene which provides for identification of whether a homologous double crossover has occurred (negative selection). The Herpes simplex virus thymidine kinase gene (HSV-tk) may be used as a negative selection marker, since cells producing thymidine kinase may be killed by acyclovir or gancyclovir.

Once a targeting construct has been prepared and any undesirable sequences removed, the construct can be introduced into the target cell, for example an ES cell or an oocyte. Any convenient technique for introducing the DNA into the target cell may be employed. For conventional gene targeting (usually constructs up to 20 kb), DNA is most frequently introduced by electroporation (see Zou et al., Eur. J. Immunol., 25, 2154-62, 1995) whilst for secondary modifications, such as Cre-loxP mediated integration, electroporation can be used for integration of smaller constructs and other methods such as lipofection and yeast spheroplast/cell fusion for YACs (yeast artificial chromosomes) and calcium phosphate-mediated DNA transfer for chromosome-fragments or mammalian artificial chromosomes which would allow integration of several 100 kb up to the Mb range. Thus, electroporation is the preferred technique for introduction of small DNA fragments (up to 50 kb) into the target cell, the other methods listed are suitable and perhaps advantageous for the introduction of larger DNA sequences (>50 kb).

After transformation or transfection of the target cells, they may be selected by means of positive and/or negative markers. As previously indicated, positive markers such as neomycin and/or puromycin resistance genes can be used. Those cells with the desired phenotype may then be further analysed by restriction analysis, electrophoresis, Southern blot analysis, PCR, or the like.

PCR may also be used to detect the presence of homologous recombination. PCR primers can be used that are complementary to a sequence within the targeting construct, and complementary to a sequence outside the construct and at the target locus. DNA molecules are obtained in the PCR reaction only when both the primers are able to bind to the complementary sequences, i.e. only if homologous recombination has occurred. Demonstration of the expected size fragments, verified by sequencing, supports the conclusion that homologous recombination has occurred.

While the presence of the marker gene in the genome indicates that integration has taken place, it is necessary to determine whether homologous integration has occurred. Methods for achieving this are known in the art, such as using DNA analysis by Southern blot hybridisation to establish the location of the integration. By employing probes for both the insert and the sequences at the 5' and 3' regions distant to the flanking region where homologous integration would occur, it can be shown that homologous targeting has been achieved. An advantage is that external probes adjacent to the targeting DNA and newly introduced restriction sites, for example by a selectable marker gene, can be used for identification of the targeted alteration.

An embryonic stem cell as described herein, e.g. obtainable by the above method, can be used for the production of a genetically modified non-human mammal.

The above-described processes may be performed first to inactivate the MASP-2 locus in an embryonic stem cell, the cells may then be injected into a host blastocyst and developed into a chimaeric animal. Suitable methods are described, for example, in Hogan et al, (Hogan, B., Beddington, R., Costantini, F., and Lacy, E. (1994). Manipulating the Mouse Embryo: A Laboratory Manual. Cold Spring Harbour Press NY). Chimaeric animals are bred to obtain heterozygous hosts. Then, by breeding of the heterozygous hosts, a homozygous host may be obtained.

Accordingly, the invention provides a method for producing a genetically modified non-human mammal characterised in that an embryonic stem cell as described herein is introduced into a host blastocyst and developed into a chimaeric animal.

This can be achieved by a method characterised by:

(a) introducing a non-human mammal embryonic stem cell as described herein into a compatible non-human mammal blastocyst, and (b) transplanting the blastocyst obtained in (a) into a compatible non-human mammalian foster mother to obtain a chimaeric non-human mammal, and optionally, screening for the selectable marker(s), and/or for deletion of all or essentially all endogenous MASP-2 gene sequences.

A chimaeric non-human mammal produced by these methods can be bred to obtain heterozygous progeny. The heterozygous progeny can be inter-bred to obtain homozygous progeny.

Using methods of the invention described herein a genetically modified non-human mammal can be obtained that does not comprise a nucleic acid sequence which itself encodes any endogenous MASP-2 polypeptide.

The invention provides a method for producing a genetically modified non-human mammal capable of expressing one or more exogenous genes, characterised by breeding a genetically modified non-human mammal that does not comprise a nucleic acid sequence which itself encodes any endogenous MASP-2 polypeptide, with a compatible non-human mammal that encodes and is capable of expressing one or more exogenous gene(s), to obtain progeny heterozygous for the one or more exogenous gene(s), and optionally inter-breeding the heterozygous progeny to produce progeny homozygous for the one or more exogenous gene(s).

An exogenous gene is a gene which is foreign, i.e. non-native, to the host non-human mammal or cell.

Thus the invention may be used to produce a non-human mammal, that is preferably a rodent, more preferably a mouse, that is capable of expressing foreign, preferably human, MASP-2 gene(s), by breeding the genetically modified non-human mammal as defined herein that is unable to express functionally active (endogenous) MASP-2 genes, with a compatible non-human mammal, preferably a rodent, more preferably a mouse, that is able to express one or more functionally active foreign, preferably human, MASP-2 genes. This enables inter-species gene/locus exchange to produce selected progeny (heterozygous or homozygous) with one or more functionally active exogenous, preferably human gene(s) of the desired traits in a background where the corresponding genes of the non-human mammal are silenced or removed. Such a non-human mammal may be useful in the production of antibodies to the exogenous gene, and the present invention further provides a method for the production of such antibodies, and antibodies produced in such a method.

As used herein, the term "antibody" encompasses antibodies and antibody fragments thereof derived from any antibody producing mammal (e.g., mouse, rat, rabbit, and primate including human) that specifically bind to MASP-2 polypeptides or portions thereof. Exemplary antibodies include polyclonal, monoclonal and recombinant antibodies, multispecific antibodies (e.g., bispecific antibodies), humanized antibodies, murine antibodies, chimeric, mouse-human, mouse-primate, human monoclonal antibodies, and anti-idiotype antibodies, and may be an intact molecule or a fragment thereof.

As used herein, the term "antibody fragments" refers to a portion derived from or related to a full length anti-MASP-2 antibody, generally including the antigen binding or variable region thereof. Illustrative examples of antibody fragments include Fab, Fab', F(ab)2, F(ab')2 and Fv fragments, scFv fragments, diabodies, linear antibodies, single-chain antibody molecules and multispecific antibodies formed from antibody fragments.

As used herein, "single-chain Fv" or "scFv" antibody fragments comprise the VH and VL domains of an antibody, wherein these domains are present in a single polypeptide chain. Generally, the Fv polypeptide further comprises a polypeptide linker between the VH and VL domains, which enables the scFv to form the desired structure for antigen binding.

As used herein, a "chimeric antibody" is a recombinant protein that contains the variable domains and complementary determining regions derived from a non-human species (e.g., rodent) antibody, while the remainder of the antibody molecule is derived from a human antibody.

As used herein, a "humanized antibody" is a chimeric antibody which comprises a minimal sequence that conforms to specific complementarity determining regions derived from non-human immunoglobulin that is transplanted into a human antibody framework. Humanized antibodies are typically recombinant proteins in which only the antibody complementarity-determining regions are of non-human origin.

Polyclonal antibodies against MASP-2 can be prepared by immunizing an animal with MASP-2 polypeptide or an immunogenic portion thereof using methods well-known to those of ordinary skill in the art. See, for example, Green et al., "Production of Polyclonal Antisera," in Immunochemical Protocols (Manson, ed.), page 105. The immunogenicity of a MASP-2 polypeptide can be increased through the use of an adjuvant, including mineral gels, such as aluminium hydroxide or Freund's adjuvant (complete or incomplete), surface active substances such as lysolecithin, pluronic polyols, polyanions, oil emulsions, keyhole limpet hemocyanin and dinitrophenol. Polyclonal antibodies are typically raised in animals such as horses, cows, dogs, chicken, rats, mice, rabbits, guinea pigs, goats, or sheep. Alternatively, an anti-MASP-2 antibody useful in the present invention may also be derived from a subhuman primate. General techniques for raising diagnostically and therapeutically useful antibodies in baboons may be found, for example, in Goldenberg et al., International Patent Publication No. WO 91/11465, and in Losman et al., Int. J. Cancer 46:310, 1990. Sera containing immunologically active antibodies are then produced from the blood of such immunized animals using standard procedures well known in the art.

In some embodiments, the MASP-2 antibody may be a monoclonal antibody. Anti-MASP-2 monoclonal antibodies are highly specific, being directed against a single MASP-2 epitope. As used herein, the modifier "monoclonal" indicates the character of the antibody as being obtained from a substantially homogenous population of antibodies, and is not to be construed as requiring production of the antibody by any particular method. Monoclonal antibodies can be obtained using any technique that provides for the production of antibody molecules by continuous cell lines in culture, such as the hybridoma method described by Kohler et al., Nature 256:495, 1975, or they may be made by recombinant DNA methods (see, e.g., U.S. Pat. No. 4,816,567). Monoclonal antibodies may also be isolated from phage antibody libraries using the techniques described in Clackson et al., Nature 352:624-628, 1991, and Marks et al., J. Mol. Biol. 222:581-597, 1991. Such antibodies can be of any immunoglobulin class including IgG, IgM, IgE, IgA, IgD and any subclass thereof.

For example, monoclonal antibodies can be obtained by injecting a suitable mammal (e.g., a BALB/c mouse) with a composition comprising a MASP-2 polypeptide or portion thereof. After a predetermined period of time, splenocytes are removed from the mouse and suspended in a cell culture medium. The splenocytes are then fused with an immortal cell line to form a hybridoma. The formed hybridomas are grown in cell culture and screened for their ability to produce a monoclonal antibody against MASP-2.

Human monoclonal antibodies may be obtained through the use of transgenic mice that have been engineered to produce specific human antibodies in response to antigenic challenge. In this technique, elements of the human immunoglobulin heavy and light chain locus are introduced into strains of mice derived from embryonic stem cell lines that contain targeted disruptions of the endogenous immunoglobulin heavy chain and light chain loci. The transgenic mice can synthesize human antibodies specific for human antigens, such as the MASP-2 antigens described herein, and the mice can be used to produce human MASP-2 antibody-secreting hybridomas by fusing B-cells from such animals to suitable myeloma cell lines using conventional Kohler-Milstein technology. Transgenic mice with a human immunoglobulin genome are commercially available (e.g., from Abgenix, Inc., Fremont, Calif., and Medarex, Inc., Annandale, N.J.). Methods for obtaining human antibodies from transgenic mice are described, for example, by Green et al., Nature Genet. 7:13, 1994; Lonberg et al., Nature 368:856, 1994; and Taylor et al., Int. Immun. 6:579, 1994.

Monoclonal antibodies can be isolated and purified from hybridoma cultures by a variety of well-established techniques. Such isolation techniques include affinity chromatography with Protein A Sepharose, size-exclusion chromatography, and ion-exchange chromatography (see, for example, Coligan at pages 2.7.1 2.7.12 and pages 2.9.1 2.9.3; Baines et al., "Purification of Immunoglobulin G (IgG)," in Methods in Molecular Biology, vol. 10, pages 79-104 (The Humana Press, Inc., 1992).

Monoclonal antibodies useful in the method of the invention include chimeric antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies (U.S. Pat. No. 4,816,567 and Morrison et al., Proc. Nat'l Acad. Sci., USA 81:6851-6855, 1984). One form of a chimeric antibody useful in the invention is a humanized monoclonal anti-MASP-2 antibody. Humanized forms of non-human (e.g., murine) antibodies are chimeric antibodies, which contain minimal sequence derived from non-human immunoglobulin. Humanized monoclonal antibodies are produced by transferring the non-human (e.g., a mouse) complementary determining regions (CDR), from the heavy and light variable chains of the mouse immunoglobulin into a human variable domain. Typically, residues of human antibodies are then substituted in the framework regions of the non-human counterparts. Furthermore, humanized antibodies may comprise residues which are not found in the recipient antibody or in the donor antibody. These modifications are made to further refine antibody performance In general, the humanized antibody will comprise substantially all of at least one, and typically two variable domains, in which all or substantially all of the hypervariable loops correspond to those of a non-human immunoglobulin and all or substantially all of the Fv framework regions are those of a human immunoglobulin sequence. The humanized antibody optionally also will comprise at least a portion of an immunoglobulin constant region (Fc), typically that of a human immunoglobulin. For further details, see Jones et al., Nature 321:522-525, 1986; Reichman et al., Nature 332: 323-329, 1988, and Presta, Curr. Op. Struct. Biol. 2:593-596, 1992.

Techniques for producing humanized monoclonal antibodies are also described, for example, by Jones et al., Nature 321:522, 1986; Carter et al., Proc. Nat'l. Acad. Sci. USA 89:4285, 1992; Sandhu, Crit. Rev. Biotech. 12:437, 1992; Singer et al., J. Immun. 150:2844, 1993; Sudhir (ed.), Antibody Engineering Protocols (Humana Press, Inc., 1995); Kelley, "Engineering Therapeutic Antibodies," in Protein Engineering: Principles and Practice, Cleland et al. (eds.), pages 399-434 (John Wiley & Sons, Inc., 1996); and by Queen et al., U.S. Pat. No. 5,693,762 (1997). In addition, there are commercial entities that will synthesize humanized antibodies from specific murine antibody regions, such as Protein Design Labs (Mountain View Calif.).

The present invention further extends not only to intact immunoglobulin molecules but also to the well-known fragments including Fab, Fab', F(ab)2, F(ab')2 and Fv fragments, scFv fragments, diabodies, linear antibodies, single-chain antibody molecules and multispecific antibodies formed from antibody fragments. It is well known in the art that only a small portion of an antibody molecule, the paratope, is involved in the binding of the antibody to its epitope (see, e.g., Clark, W. R. (1986) The Experimental Foundations of Modern Immunology, Wiley & Sons, Inc., NY). The pFc' and Fc regions of the antibody are effectors of the classical complement pathway, but are not involved in antigen binding. An antibody from which the pFc' region has been enzymatically cleaved, or which has been produced without the pFc' region is designated an F(ab')2 fragment and retains both of the antigen binding sites of an intact antibody. An isolated F(ab')2 fragment is referred to as a bivalent monoclonal fragment because of its two antigen binding sites. Similarly, an antibody from which the Fc region has been enzymatically cleaved, or which has been produced without the Fc region, is designated a Fab fragment, and retains one of the antigen binding sites of an intact antibody molecule.

Antibody fragments can be obtained by proteolytic hydrolysis, such as by pepsin or papain digestion of whole antibodies by conventional methods. For example, antibody fragments can be produced by enzymatic cleavage of antibodies with pepsin to provide a 5S fragment denoted F(ab')2. This fragment can be further cleaved using a thiol reducing agent to produce 3.5S Fab' monovalent fragments. Optionally, the cleavage reaction can be performed using a blocking group for the sulfhydryl groups that result from cleavage of disulfide linkages. As an alternative, an enzymatic cleavage using pepsin produces two monovalent Fab fragments and an Fc fragment directly. These methods are described, for example, by Goldenberg, U.S. Pat. No. 4,331,647; Nisonoff et al., Arch. Biochem. Biophys. 89:230, 1960; Porter, Biochem. J. 73:119, 1959; Edelman et al., in Methods in Enzymology, 1:422 (Academic Press 1967); and by Coligan at pages 2.8.1 2.8.10 and 2.10. 2.10.4.

In some embodiments, the use of antibody fragments lacking the Fc region are preferred to avoid activation of the classical complement pathway which is initiated upon binding Fc to the Fcγ receptor. There are several methods by which one can produce a MAb that avoids Fcγ receptor interactions. For example, the Fc region of a monoclonal antibody can be removed chemically using partial digestion by proteolytic enzymes (such as ficin digestion), thereby generating, for example, antigen-binding antibody fragments such as Fab or F(ab)2 fragments (Mariani, M et al., Mol. Immunol. 28:69-71, 1991). Alternatively, the human γ4 IgG isotype, which does not bind Fcγ receptors, can be used during construction of a humanized antibody as described herein. Antibodies, single chain antibodies and antigen-binding domains that lack the Fc domain can also be engineered using recombinant techniques described herein.

Alternatively, one can create single peptide chain binding molecules specific for MASP-2 in which the heavy and light chain Fv regions are connected. The Fv fragments may be connected by a peptide linker to form a single chain antigen binding protein (scFv). These single-chain antigen binding proteins are prepared by constructing a structural gene comprising DNA sequences encoding the VH and VL domains which are connected by an oligonucleotide. The structural gene is inserted into an expression vector, which is subsequently introduced into a host cell, such as E. coli. The recombinant host cells synthesize a single polypeptide chain with a linker peptide bridging the two V domains. Methods for producing scFvs are described for example, by Whitlow et al., "Methods: A Companion to Methods" in Enzymology 2:97, 1991; Bird et al., Science 242:423, 1988; Ladner et al., U.S. Pat. No. 4,946,778; and Pack et al., Bio/Technology 11:1271, 1993.

A method is provided for producing a genetically modified non-human mammal or cell capable of expressing one or more exogenous gene(s) comprising introduction of one or more exogenous gene(s) into a non-human mammalian cell as described herein that does not comprise a nucleic acid sequence which itself encodes any endogenous MASP-2 polypeptide. It is preferred that the non-human mammalian cell is an embryonic stem cell or an oocyte. When the non-human mammalian cell is an ES cell, it is preferred that the one or more exogenous gene(s) are introduced by transfection. When the non-human mammal cell is an oocyte (egg cell) it is preferred that the one or more exogenous gene(s) are introduced by DNA micro-injection. Preferably the one or more exogenous gene(s) are inserted into the genome of the non-human mammal or cell, most preferably the one or more exogenous gene(s) are inserted into a non-endogenous site specific recombination sequence.

The invention provides a non-human mammal or cell capable of expressing one or more exogenous genes, obtainable by a method described herein and provides the use of a non-human mammal or cell in the production of exogenous MASP-2, preferably human MASP-2.

Also provided by the present invention is a genetically modified non-human mammal or a genetically modified non-human mammalian cell characterised in that it does not comprise a nucleic acid sequence which itself encodes an endogenous MAp 19 polypeptide. Such a mammal may be useful for the same or similar purposes, and in the same or similar manner, as the MASP-2 deficient genetically modified non human mammals described above. Unless otherwise stated, therefore, the skilled person will understand that the above statements relating to MASP-2 deficient mammals, and to antibodies and other products obtainable from such mammals, and to methods involving such mammals, are equally applicable to MAp 19 deficient mammals.

The present invention further provides a genetically modified non human mammal or a genetically modified non human mammalian cell characterised in that it lacks a lectin complement pathway response.

A genetically modified non-human mammal of the invention can be rodent, murine, ovine, porcine, equine, canine, feline or the like, but is preferably a rodent, more preferably murine, most preferably a mouse. A genetically modified non-human mammalian cell of the invention may be an embryonic stem cell or an oocyte; and is preferably a rodent, murine, ovine, porcine, equine, canine or feline cell, or the like, preferably a rodent cell, more preferably a murine cell, most preferably a mouse cell. Mice are particularly preferred as they are easy to handle and breed.

The present invention provides a mouse in which no functional lectin complement pathway response is present.

BRIEF DESCRIPTION OF THE DRAWINGS

FIG. 10A shows the nucleotide sequence (nucleotides 1 to 2957 of SEQ ID NO 1) of the MASP-2 minigene construct of FIG. 4A and FIG. 10B shows the nucleotide sequence (nucleotides 2958 to 4960 of SEQ ID NO:1) of the MASP-2 minigene construct of FIG. 4A.

FIG. 11A shows the nucleotide sequence (nucleotides 1 to 2957 of SEQ ID NO 2) of the MAp19 minigene construct of FIG. 4B and FIG. 11B shows the nucleotide sequence (nucleotides 2958 to 3236 of SEQ ID NO:2) of the MAp 19 minigene construct of FIG. 4B.

DETAILED DESCRIPTION OF THE DRAWINGS

Figure 1:
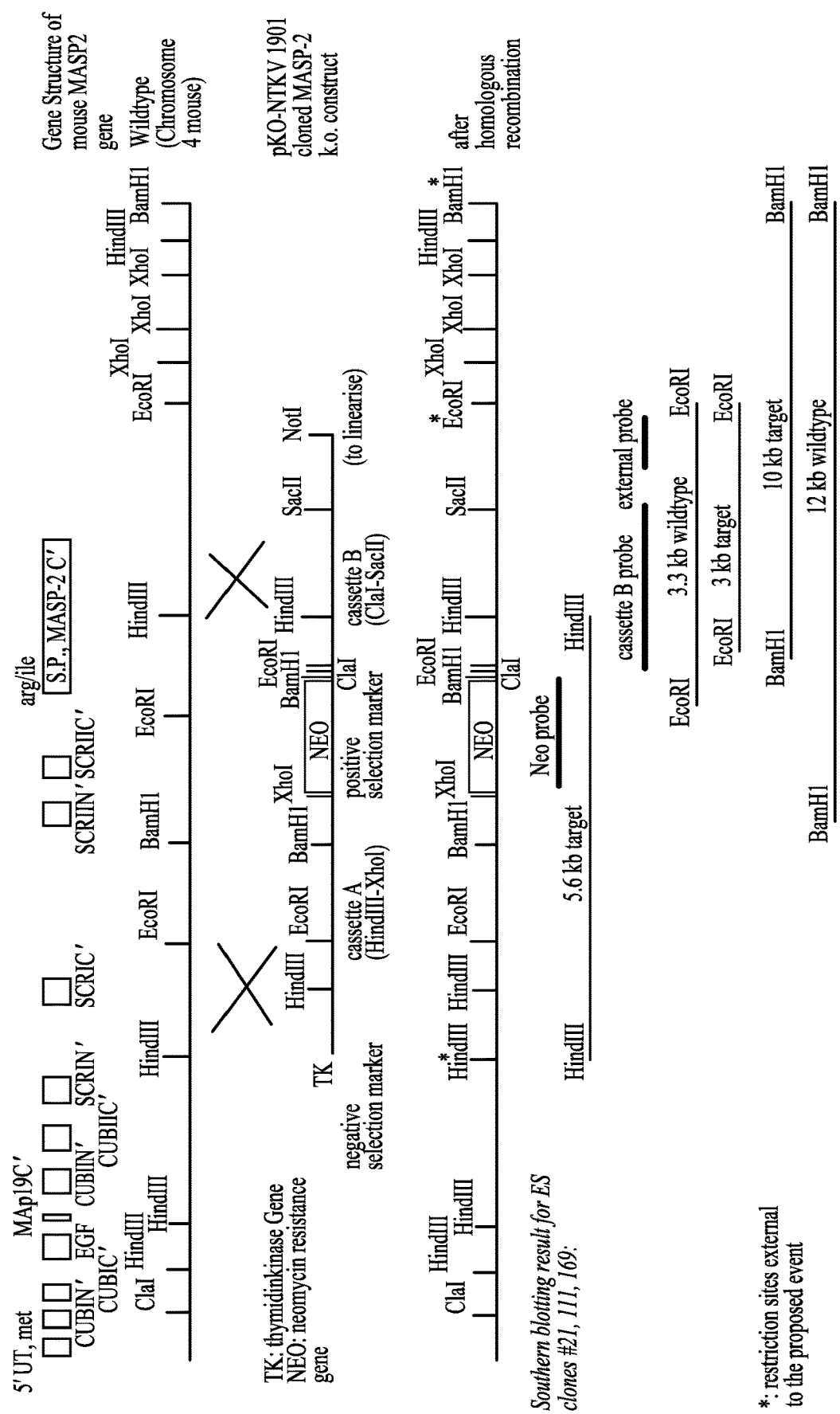
FIG. 1 shows a map indicating targeting of murine MASP-2 for knockout experiments, together with a construct used for MASP-2 knockout, in accordance with an embodiment of the present invention.
Figure 2:
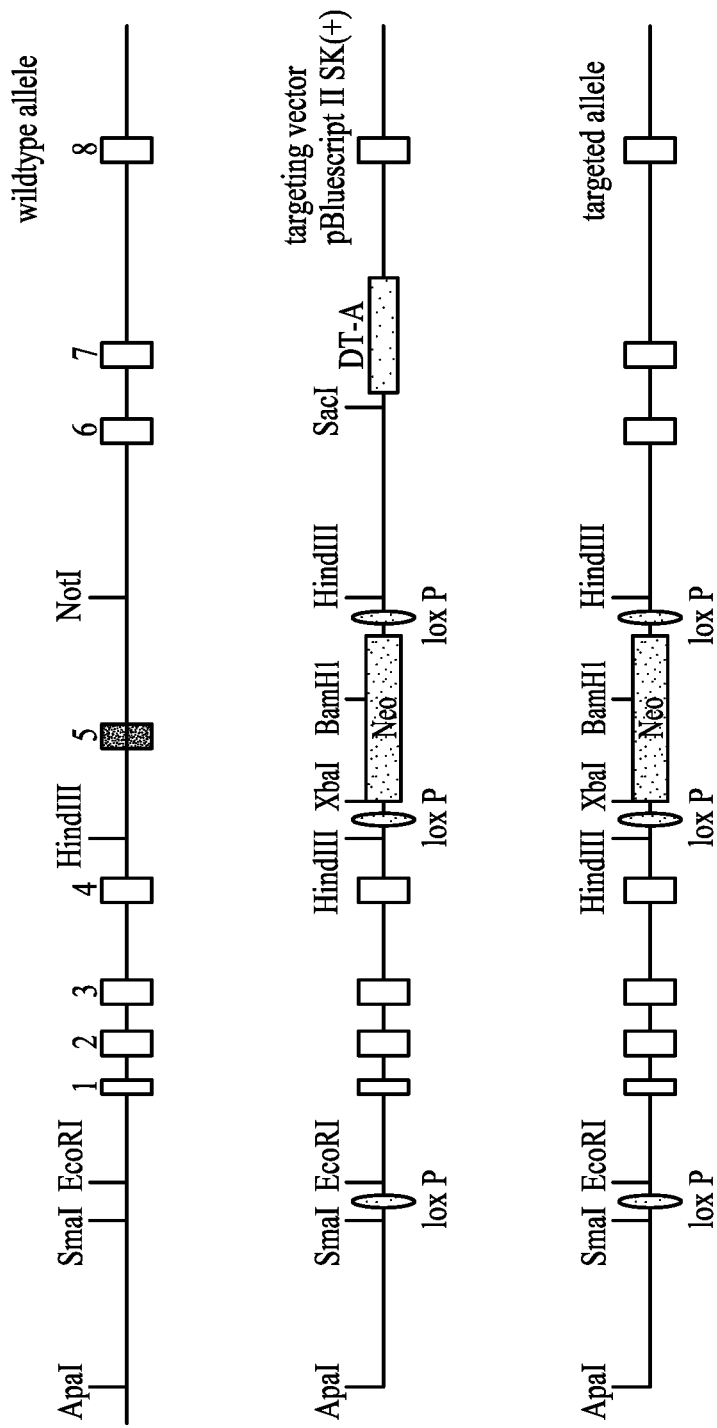
FIG. 2 shows a loxP construct useful for targeting MAp19 (as exon 5 of the murine MASP-2 gene) for knockout experiments, in accordance with an embodiment of the present invention, useful in the generation of a MAp19 deficient/MASP-2 sufficient mammal.
Figure 3:
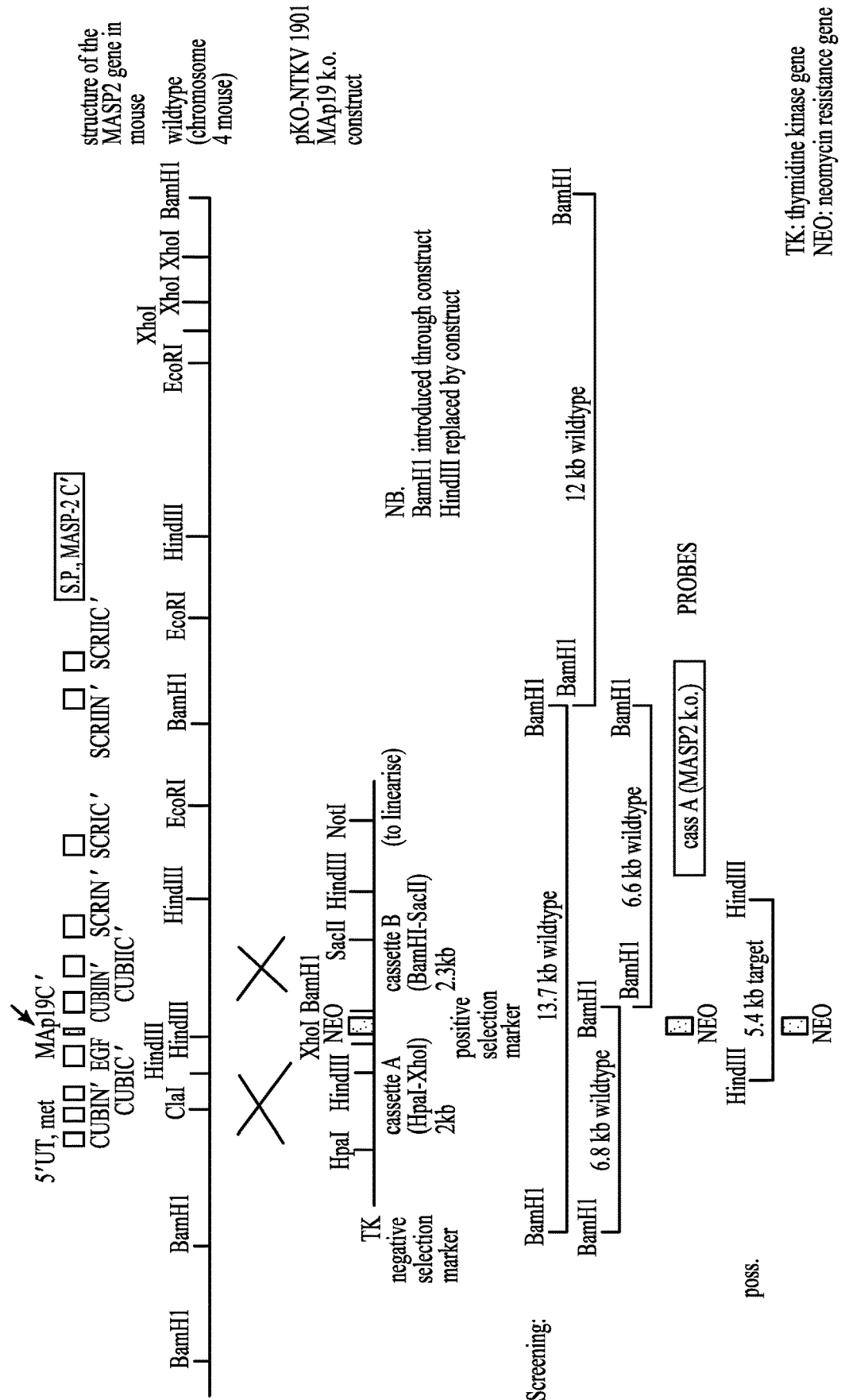
FIG. 3 shows an alternative construct useful for targeting MAp19 for knockout experiments, useful in the generation of a MAp19 and MASP-2 deficient mammal.

FIGS. 1, 2 and 3 show maps indicating targeting of mouse MASP-2 and MAp19 knockouts, and show constructs used in the targeting. FIG. 4 shows minigene constructs used for introduction of human MASP-2 and MAp19 genes into knockout mice. The mRNA sequence of mouse MASP-2 is available under GenBank accession number BC013893.

The present inventors have generated 5 different mouse strains by either gene targeting and/or transgene technology. These lines are designed to be selectively sufficient for either the murine MASP2 gene products MASP-2 (i.e. the serine protease (MW 74095 Da) of the lectin pathway of complement) and/or MAp19 (also called sMAP) (i.e. the alternative MASP2 gene product of 19075 Da MW associated with lectin pathway initiation complexes). We describe three lines with deficiencies of murine MASP-2 gene products: a line deficient of the serine protease MASP-2, but sufficient of Map19/sMAP (construct shown in FIG. 1), a line deficient of MAp19/sMAP (construct shown in FIG. 2), and a line deficient of both MASP-2 and MAp19/sMAP (construct shown in FIG. 3).

Confirmation of deficiencies was carried out by detection of mRNA transcripts and/or Western blotting experiments. Nucleic acid detection was determined by time-resolved RT-PCR using a LightCycler instrument, while findings were confirmed by Western blotting.

In addition, two human minigene constructs were established (see FIGS. 4A and 4B) to express human MASP-2 or human MAp19 in the knockout mice.

Referring to MASP-2 for now, the construct of FIG. 1 was established in the gene-targeting vector pKO-NTKV 1901 (Stratagene, CA) and used to transfect the murine ES cell line E14.1a (genetic background SV129 Ola). Transfected cells which integrated the construct in their chromosomal DNA were selected through Neomycin-resistance and the recombination event selected through loss of the Thymidine Kinase (TK) activity mediated by the TK gene contained in pKO-NTKV. From 600 ES cell clones harvested after transfection, the single integration of the gene targeting construct and the targeting event within the murine MASP2 gene were verified by Southern Blot analysis using hybridisation probes specific for the Neomycin cassette contained in the targeting construct and probe specific for the murine MASP2 gene located outside of the targeting construct. We identified 4 different cell clones in which a selective targeting and recombination event occurred and used these to create chimeras by embryo-transfer-technology in the Transgenic Unit at the University of Leicester. Chimeras were backcrossed on the genetic background C57/BL6 and created transgenic males that transmitted the disrupted gene in their germ-line. Mating such "germ-line transmitting" mice with females (genetic background C57/BL6) generated an F1 with 50% of the offspring showing heterozygosity for the disrupted MASP2 gene. These heterozygous mice were intercrossed generating homozygous MASP2 deficient offspring, heterozygous and wildtype mice in the ratio 1:2:1, respectively.

The first MASP-2 deficient mouse line (from now on termed MASP2 −/−CS) was established using the targeting construct described in FIG. 1. The strategy chosen disrupts three exons (exons 10, 11, and 12) coding for the C-terminal end of MASP-2, including the exon that encodes the serine protease domain, but the disruption is far distant from the exons encoding the other MASP2 gene product MAp19/sMAP.

The resulting murine strain, MASP2 −/− CS generated with the disruption construct described in FIG. 1 is fertile and viable and contains a targeted deficiency for MASP-2 when homozygous for the disrupted allele. MAp19/sMAP, the alternative gene product of the MASP2 gene is present on both the mRNA and the protein level (determined by RT-PCR and Western blotting). These mice express the other two lectin pathway associated serine proteases, i.e. MASP-1 and MASP-3.

Figure 5A:
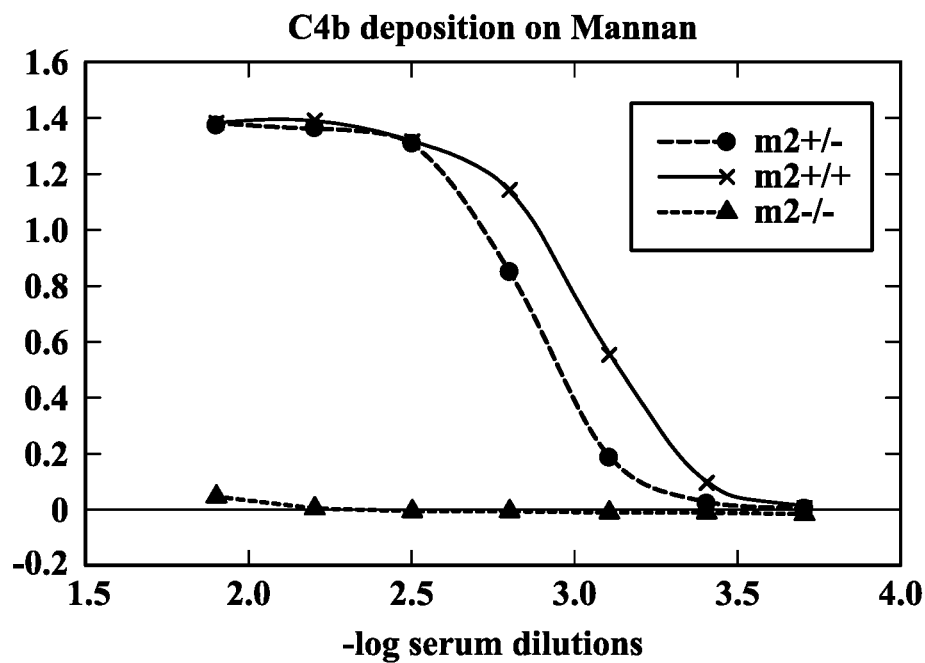
FIGS. 5A and 5B show the results of experiments indicating that MASP-2 deficient mice lack lectin pathway mediated C4 activation.
Figure 5B:
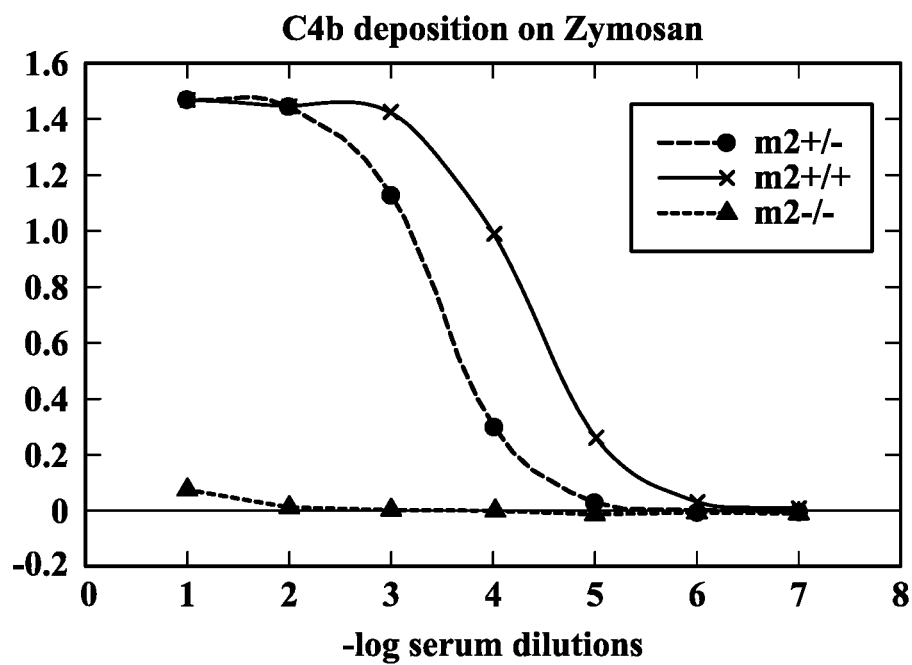

As shown in FIGS. 5A and 5B, plasma of MASP2 −/− CS mice is totally deficient of lectin pathway mediated complement activation on mannan (FIG. 5A) and on zymosan (FIG. 5B) coated plates as shown in the lectin pathway specific C4 cleavage assay. This clearly demonstrates that MASP-2, but not MASP-1 or MASP-3, is the effector component of the lectin pathway of complement activation. MASP-1 and MASP-3 cannot compensate for the loss of MASP-2 functional activity to maintain residual lectin pathway activity under physiological condition. This result and the previously described observations of Professor Teizo Fujita's research team (which generated a gene targeted murine strain deficient of MASP-1 and MASP-3 with no deficiency in lectin pathway mediated complement activation) demonstrates that MASP-1 and MASP-3 are only marginally if at all involved in activation of the complement system.

Figure 6A:
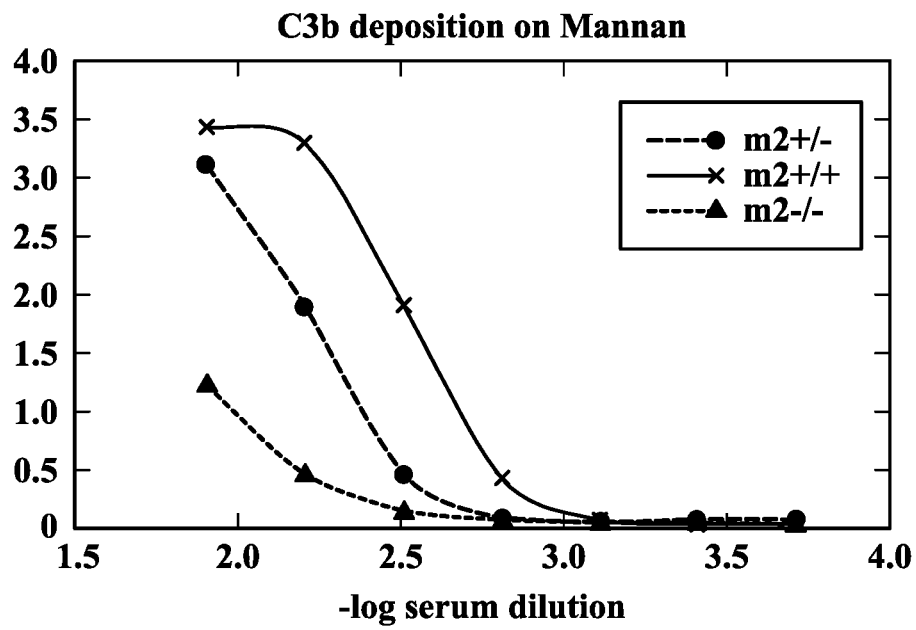
FIGS. 6A and 6B show the results of experiments indicating that MASP-2 deficient mice lack lectin pathway mediated C3 activation.
Figure 6B:
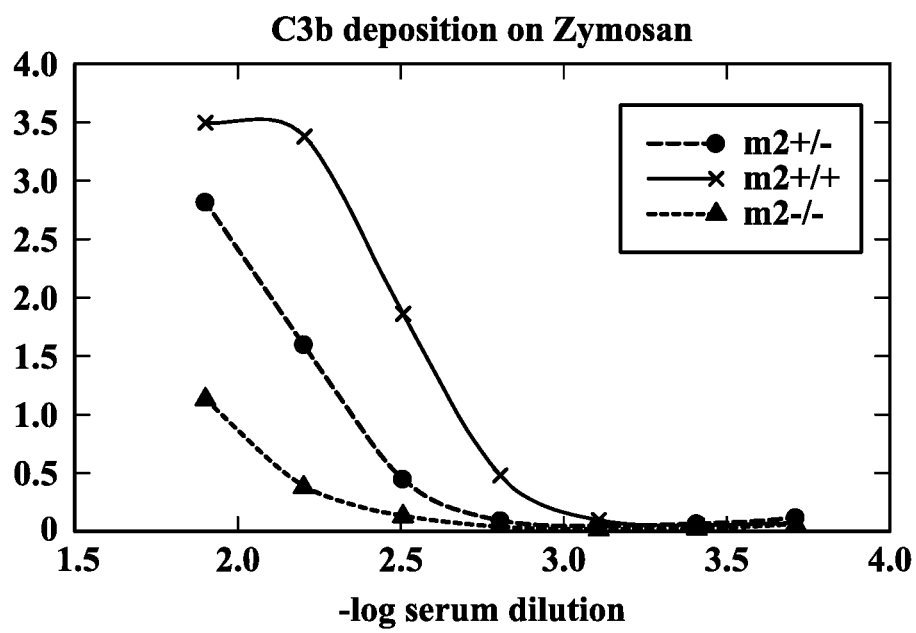

Another fundamental finding achieved by analyzing plasma of MASP2 −/− CS mice is shown in FIGS. 6A and 6B. MASP2 −/− CS mice were analysed for the presence of complement factors C3, factor B, factor D, and properdin which according to the present textbook knowledge— should form a functional active third pathway of complement activation, i.e. the alternative pathway which will cleave C3 independently of the other two pathways on activation surfaces like zymosan. As shown in FIGS. 6A and 6B, in plasma deficient of MASP-2, no or only marginal C3 activation occurs on mannan (FIG. 6A) and on zymosan (FIG. 6B) coated plates as shown by C3b deposition. This clearly demonstrates that MASP-2 is required to contribute the initial C3b to initiate the alternative pathway. In absence of MASP-2, no initial C3b is provided by the lectin pathway and even on zymosan, an established activator surface of alternative pathway activation, no alternative pathway mediated cleavage of C3 can be observed. The marginal cleavage activity seen at high concentrations of MASP-2 deficient serum could result from a residual classical pathway activity under the experimental conditions used.

Figure 7:
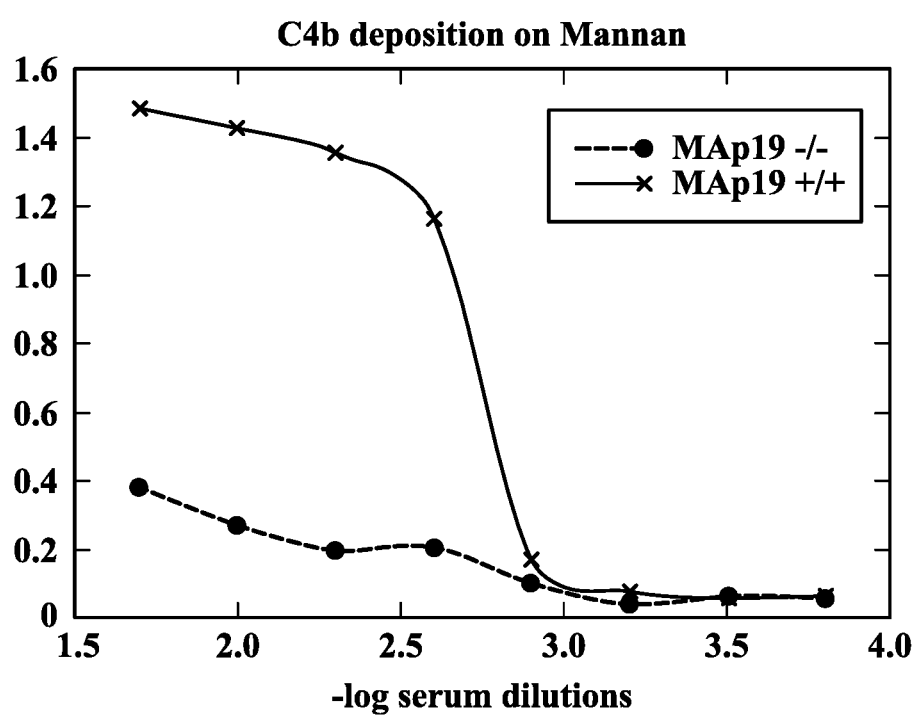
FIG. 7 shows the results of experiments indicating that MAp19 deficient mice lack lectin pathway mediated C4 activation.

The C3 and C4 cleavage assays used in obtaining the data shown in FIGS. 5 to 7 are described in Lynch, N.J.; Roscher, S.; Hartung, T., Morath, S.; Matsushita, M.; Maennel, D. N.; Kuraya, M.; Fujita, T.; Schwaeble W. J. L-ficolin Specifically Binds to Lipoteichoic Acid, a Cell Wall Constituent of Gram-positive Bacteria, and Activates the Lectin Pathway of Complement. J. Immunol. 172: 1198-1202 (2004); and Petersen S V, Thiel S, Jensen L, Steffensen R, Jensenius J C. An assay for the mannan-binding lectin pathway of complement activation. J Immunol Methods. 257: 107-116 (2001).

Figure 12:
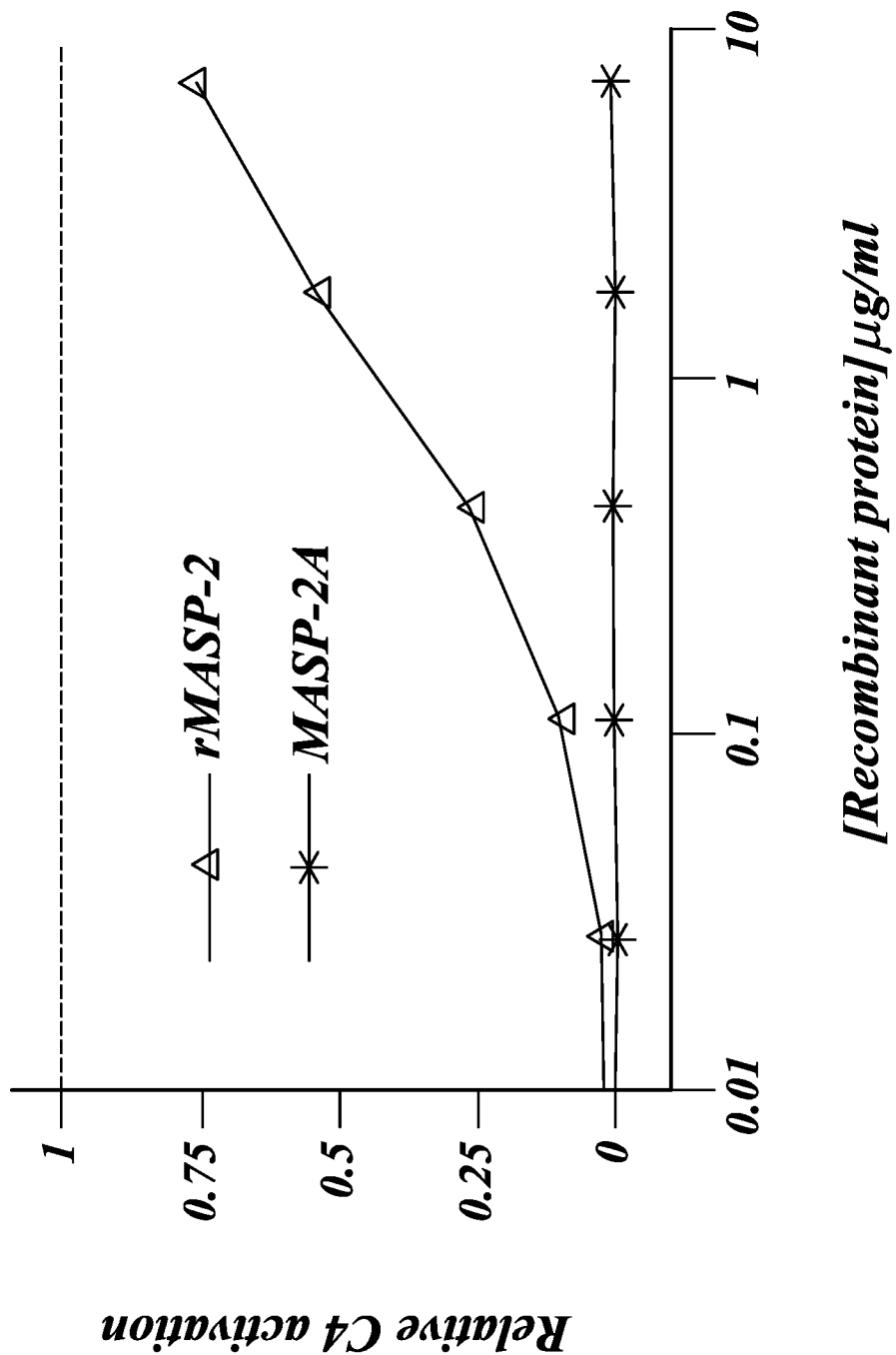
FIG. 12 shows the results of an experiment indicating that recombinant MASP-2 protein reconstitutes lectin pathway-mediated C4 activation in MASP-2 deficient mice.

In order to establish that the absence of MASP-2 was the direct cause of the loss of lectin pathway-dependent C4 activation in the MASP2 −/− CS mice, the effect of adding recombinant MASP-2 protein to serum samples was examined in the C4 cleavage assay. Functionally active murine MASP-2 and catalytically inactive murine MASP-2A (in which the active-site serine residue in the serine protease domain was substituted for an alanine residue) recombinant proteins were generated as described in J. Endotoxin Res. 11(1):47-50 (2005). Pooled serum from 4 MASP2 −/− CS mice was pre-incubated with increasing protein concentrations of recombinant murine MASP-2 or inactive recombinant murine MASP-2A and C4 convertase activity was assayed as described above. As shown in FIG. 12, the addition of functionally active murine recombinant MASP-2 protein (shown as open triangles) to serum obtained from the MASP2 −/− CS mice restored lectin pathway-dependent C4 activation in a protein concentration dependent manner, whereas the catalytically inactive murine MASP-2A protein (shown as stars) did not restore C4 activation. The results shown in FIG. 12 are normalized to the C4 activation observed with pooled normal mouse serum (shown as a dotted line).

Figure 13:
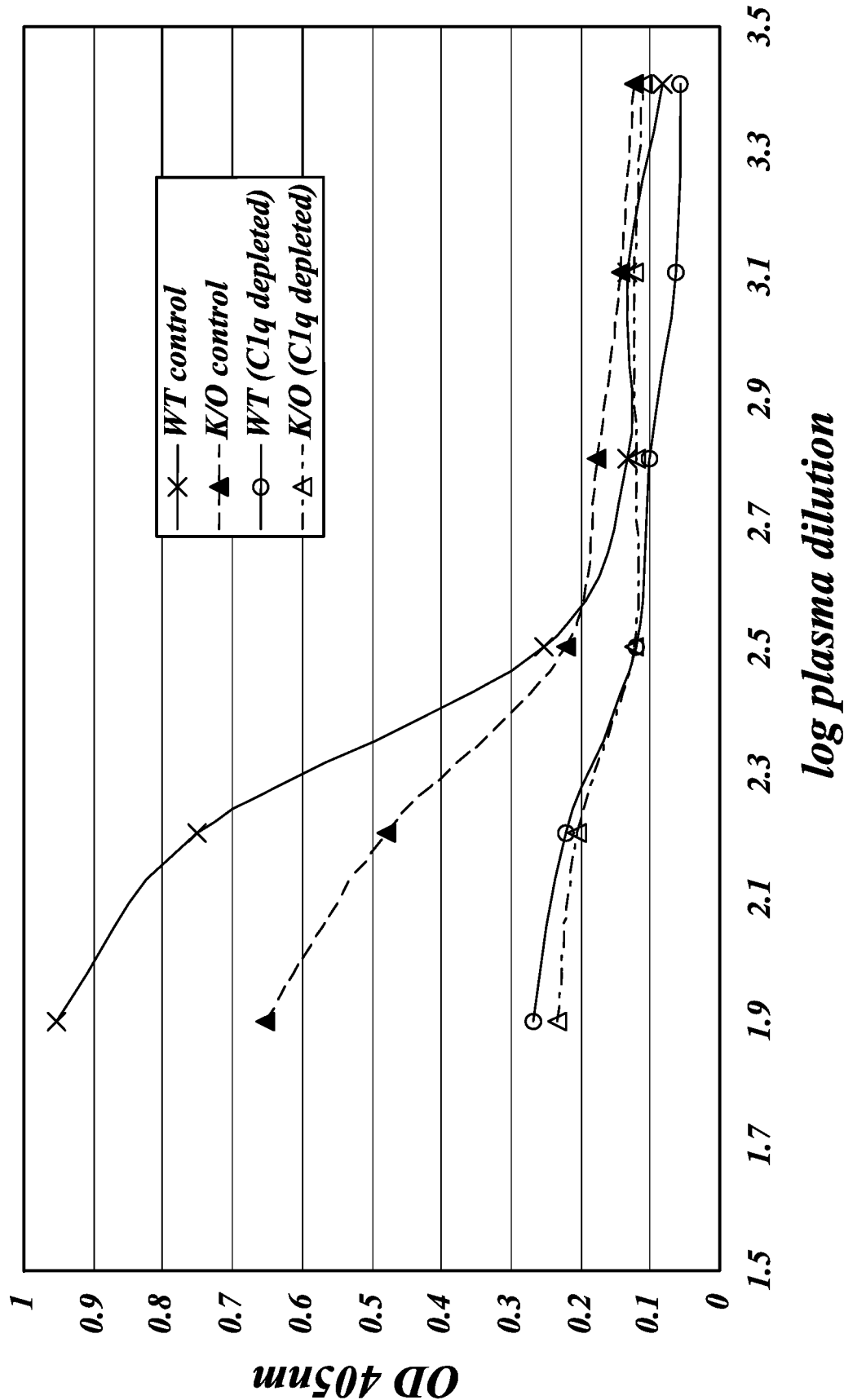
FIG. 13 shows the results of an experiment indicating that the classical pathway is functional in MASP-2 deficient mice.

FIG. 13 demonstrates that the classical pathway is functional in MASP2 −/− CS mice. In this experiment untreated and C1q depleted serum samples obtained from wild-type and MASP2 −/− CS mice were each added to plates coated with immune complexes (generated in situ by adding BSA and then adding rabbit anti-BSA). Bound C3b was detected with an anti-C3c antibody. As shown in FIG. 13, the C3b deposition was C1q-dependent in both the wild-type (C1q depleted wild-type serum is shown as open circles) and the MASP2 −/− CS mice (C1q depleted MASP2 −/− CS serum is shown as open triangles). The wild-type control serum (shown as crosses) and the MASP2 −/− CS serum (shown as closed triangles) both support C3 activation as shown by C3b deposition.

The second MASP2 gene targeted murine strain was established using the gene disruption construct described in FIG. 2. In order to generate a murine strain deficient of MAp19/sMAP, but sufficient of MASP-2, exon 5, the exon responsible for the generation of the MAp19/sMAP specific mRNA transcript of the MASP2 gene was replaced by a Neomycin cassette, flanked by loxP sites. The gene targeting construct was used to transfect an embryonic stem cell line derived from the BALB/c mouse strain. After selection for neomycin resistance, to identify transformants, the Cre/loxP system is used to excise the marker gene between the loxP sequences of the construct. This results in a mouse lacking exon 5 of MASP-2, and without a marker gene disrupting the remaining exons. The mouse is thus designed to be deficient for MAp19 (since exon 5 is absent), but expected to be sufficient for MASP-2 (since the remaining exons are present and the gene is not disrupted). We note, however, that the protein expression of MASP-2 is reduced in the Map19 deficient mice, as determined by Western blot (data not shown). The MAp19/sMAP deficient murine strain generated when homozygous for the disrupted allele is fertile and viable and will from now on be termed as MAp19/sMAP −/− TF.

FIG. 7 shows the results of an experiment indicating that the MAp19/sMAP −/− TF mouse is deficient of lectin pathway mediated complement activation on mannan coated plates. The same assay as used for FIG. 5 was used in this experiment.

The third MASP2 gene targeted murine strain was established using the gene disruption construct described in FIG. 3, in the same manner as for the MASP-2 deficient mouse described above. In order to generate a murine strain deficient of MAp19/sMAP and MASP-2, exon 5, the exon responsible for the generation of the MAp19/sMAP specific mRNA transcript of the MASP2 gene was replaced by a Neomycin cassette. Unlike the construct described with reference to FIG. 2, the construct of FIG. 3 does not include loxP sequences. The marker gene used cannot therefore be excised, and so the resulting mouse strain lacks exon 5 of MASP-2, but the remaining MASP-2 exons are disrupted by the presence of the marker gene. The resulting mouse is therefore deficient in both MAp19 and MASP-2. The gene targeted murine line created using this construct will from now on be termed MASP-2/MAp19 −/−.

Figure 4A:
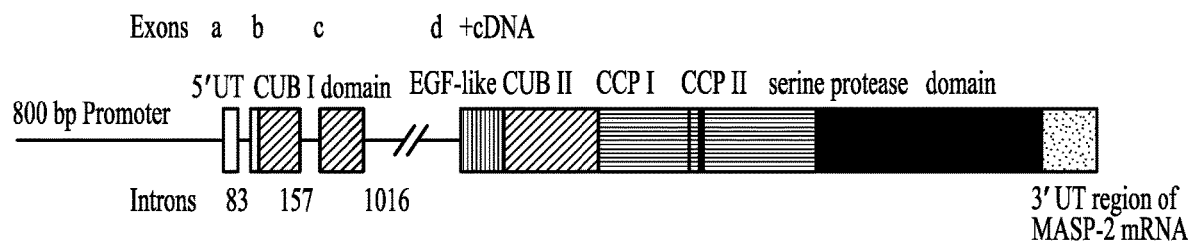
FIG. 4A shows human MASP-2 and FIG. 4B shows human MAp19 minigene constructs used for generation of transgenic animals.
Figure 4B:
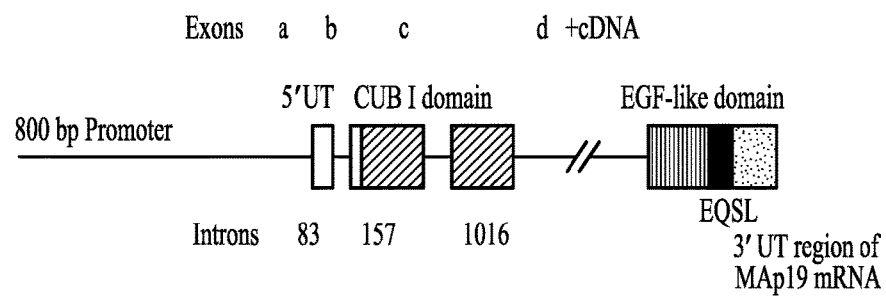

In order to replace either the deficient murine MASP-2 and/or the deficient murine MAp19 with either human MASP-2 or human MAp19, two minigene constructs were established as described in FIGS. 4A and 4B. FIG. 4A describes the minigene construct encoding human MASP-2 that uses the promoter region of the human MASP-2 gene, including the first 3 exons (exon 1 to exon3) followed by the cDNA sequence that represents the coding sequence of the following 8 exons, thereby encoding the full-length of the MASP-2 serine protease. This minigene construct, termed mini hMASP-2 was injected into fertilized eggs of MASP-2 −/− CS in order to replace the deficient murine MASP-2 gene by transgenically expressed human MASP-2. The sequence of the MASP-2 minigene construct (SEQ ID NO 1) is given in FIGS. 10A and 10B.

FIG. 4B describes the minigene construct encoding human MAp19/sMAP that uses the promoter region of the human MASP-2 gene, including the first 3 exons (exon1 to exon3) followed by the cDNA sequence that represents the coding sequence of the following 2 exons, thereby encoding the full-length of MAp19. This minigene construct, termed mini hMAp19 was injected into fertilized eggs of MASP-2 −/− CS in order to replace deficient murine MAp19 by transgenically expressed human MAp19. The sequence of the MAp19 construct (SEQ ID NO 2) is given in FIGS. 11A and 11B.

The first part of the sequence given in both FIG. 10A (nucleotides 1 to 2957 of SEQ ID NO:1) and 11A (nucleotides 1 to 2957 of SEQ ID NO:2) represents the promoter of human MASP-2 and the first three exons, and is identical in both constructs. The second part of each sequence represents the cDNA coding sequence of either the following 8 exons (FIG. 10B, nucleotides 2958 to 4960 of SEQ ID NO:1) or the following 2 exons (FIG. 11B, nucleotides 2958 to 3236 of SEQ ID NO:2). The relevant peptide sequence is also given in FIG. 11B, while the coding part of FIG. 10B is given in upper case.

A MASP 2 −/− knockout mouse expressing human MASP 2 for use as a model in which to screen for MASP-2 inhibitory agents may be produced as follows. A MASP 2 −/− mouse as described above and a MASP 2 −/− mouse expressing a human MASP 2 transgene construct (human MASP 2 knock-in) as described above are crossed, and progeny that are murine MASP-2 −/−, murine MAp19+, human MASP-2+ are used to identify human MASP-2 inhibitory agents.

Such animal models can be used as test substrates for the identification and efficacy of MASP-2 inhibitory agents such as human anti-MASP-2 antibodies, MASP-2 inhibitory peptides and nonpeptides, and compositions comprising MASP-2 inhibitory agents. For example, the animal model is exposed to a compound or agent that is known to trigger MASP-2 dependent complement activation, and a MASP-2 inhibitory agent is administered to the animal model at a sufficient time and concentration to elicit a reduction of disease symptoms in the exposed animal.

In addition, the murine MASP-2 −/−, MAp19+, human MASP-2+ mice may be used to generate cell lines containing one or more cell types involved in a MASP-2 associated disease which can be used as a cell culture model for that disorder. The generation of continuous cell lines from transgenic animals is well known in the art, for example see Small, et al., Mol. Cell Biol., 5: 642-48 (1985).

Figure 8:
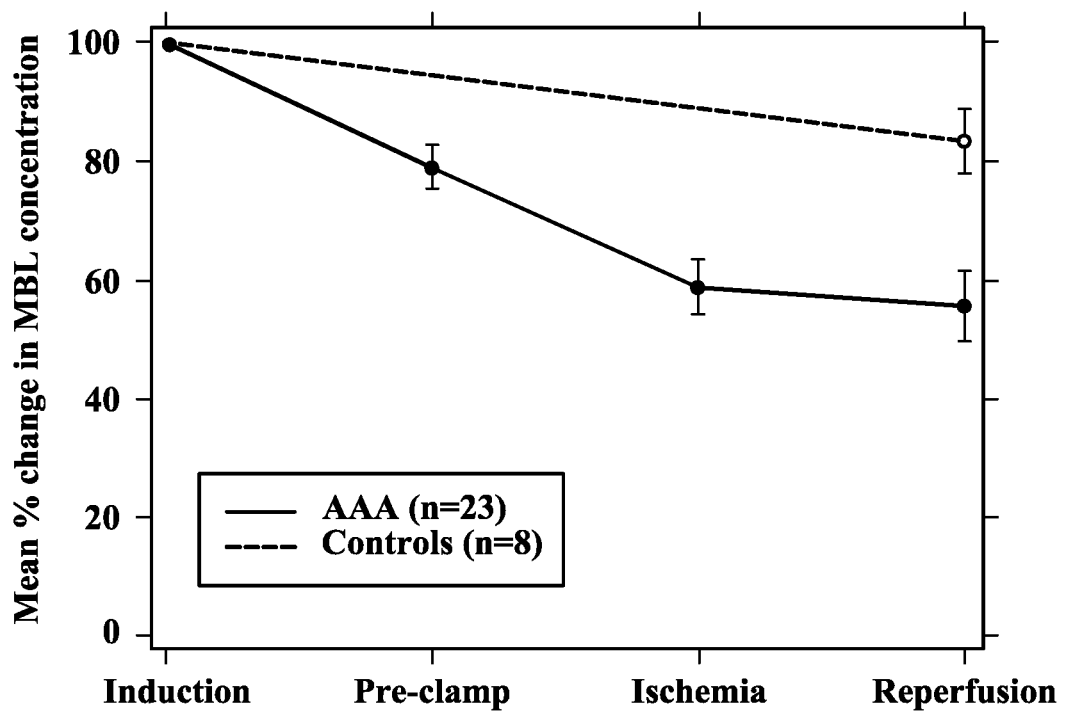
FIG. 8 is a graph showing change in MBL levels in patients having ischaemic reperfusion injuries.

Results of an experiment demonstrating that the lectin dependent MASP-2 complement activation system is activated in the reperfusion phase following abdominal aortic aneurysm repair are shown in FIG. 8. This is a graph illustrating change in MBL levels in patients having ischaemic reperfusion injuries. Patients undergoing abdominal aortic aneurysm (AAA) repair are subjected to an ischaemia reperfusion injury, which is to a large extent mediated by complement activation. We investigated the role of the lectin pathway of complement in ischaemia-reperfusion injury in patients undergoing AAA repair.

Patients undergoing elective infrarenal AAA repair had systemic blood samples taken from their radial artery (via an arterial line) at four defined time points during the procedure (Time point 1: induction of anaesthesia, Time point 2: just prior to aortic clamping, Time point 3: just prior to aortic clamp removal and Time point 4: during reperfusion). Patients undergoing major abdominal surgery were used as controls, and had blood samples taken at induction and at two hours after the start of the procedure. Patients' plasma was assayed for levels of mannan-binding lectin (MBL) using ELISA techniques. MBL is a plasma pattern recognition molecule that initiates lectin pathway activation through activation of the MBL associated serine protease MASP-2. We have used the consumption of plasma MBL as a parameter for lectin pathway activation occurring during reperfusion.

Results are illustrated in FIG. 8. 23 patients undergoing AAA repair and 8 control patients were recruited. While only a minor consumption of MBL was observed in the plasma samples taken from the control group undergoing major abdominal surgery, AAA patients show a significant decrease in plasma MBL levels—averaging at approximately 41%.

The data presented provide a strong indication that the lectin pathway of the complement system is activated in the reperfusion phase following AAA repair. This appears to be secondary to ischaemia-reperfusion injury as control sera of patients undergoing major abdominal surgery without a major ischaemia-reperfusion insult only show a slight decrease in MBL plasma levels. In light of the well established contribution of complement activation in reperfusion injury, we conclude that activation of the lectin pathway on ischaemic endothelial cells is a major factor in the pathology of reperfusion injury and that a specific transient blockade of lectin pathway activity would have a significant therapeutic impact on the outcome of disease in procedures that involve a transient ischaemic insult, i.e. myocardial infarction, gut infarction, burns, transplantation and stroke. These results also confirm that organisms deficient in the lectin pathway would be very useful as model organisms for the study of the pathway, or for the development of treatments for ischaemic injuries.

Figure 9:
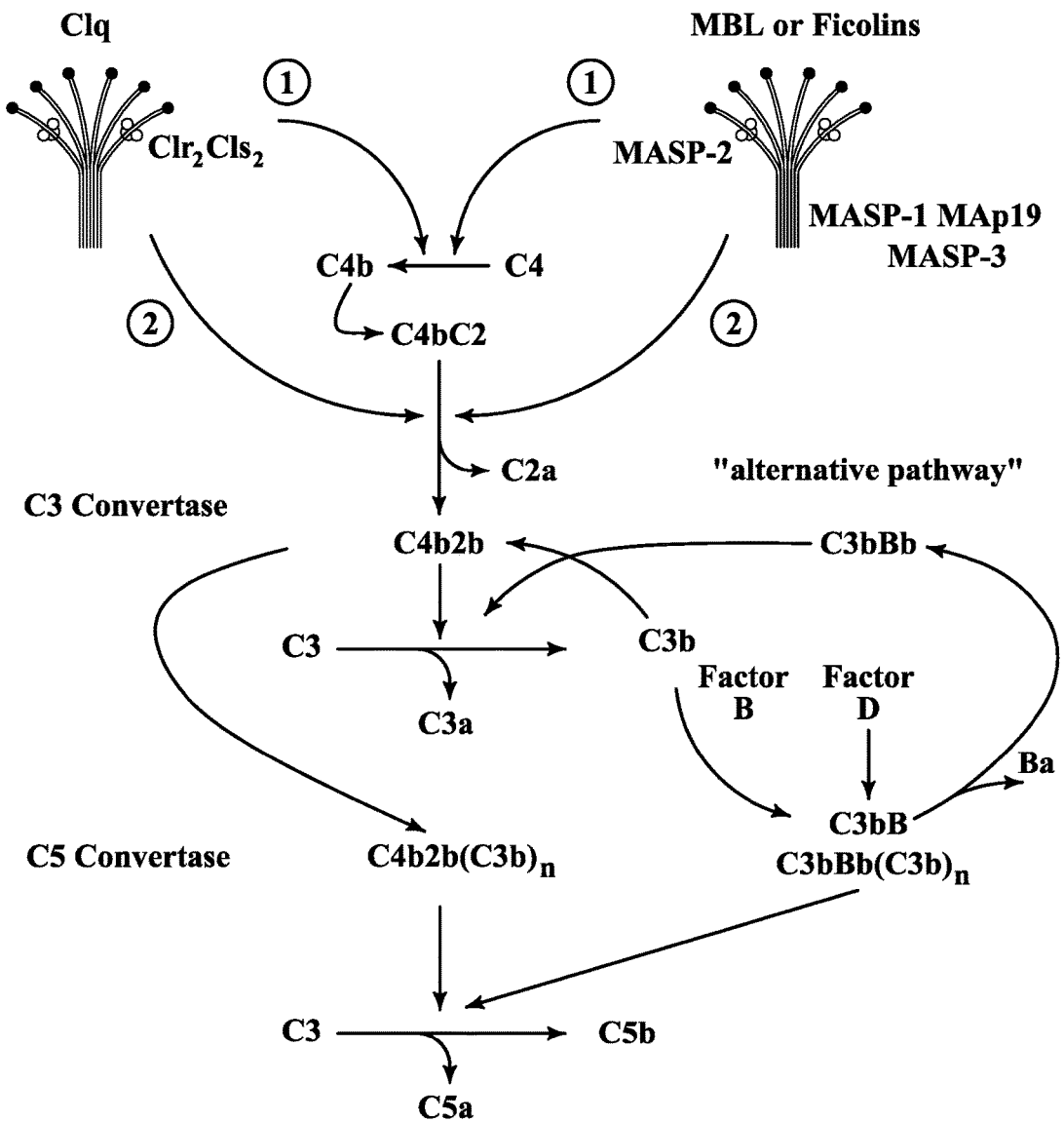
FIG. 9 is a flow chart summarising the results drawn from the experiments with MASP-2 and MAp-19 deficient mice described in FIGS. 5, 6 and 7.

Finally, FIG. 9 is a flowchart summarising the relevant lectin pathways based on the information obtained from the experiments described herein. The present inventors have identified that MASP 2 is needed to initiate alternative complement pathway activation. Through the use of a knockout mouse model of MASP 2 −/−, the present inventors have shown that it is possible to inhibit C3b deposition, the initiating step in alternative complement pathway activation via the lectin-dependent MASP-2 pathway, while leaving the classical pathway intact, thus establishing lectin-dependent MASP 2 activation as a requirement for alternate complement activation in the absence of classical pathway involvement. The present invention thus suggests the use of MASP-2 as a therapeutic target for inhibiting cellular injury associated with lectin-mediated alternate complement pathway activation, while leaving the classical (C1 q-dependent) pathway component of the immune system intact.

Furthermore, MASP-2 mediated complement activation via the lectin pathway having now been established as a requirement for the initiation of the alternative activation pathway in the absence of classical pathway involvement, the inventors have extended the present findings further that MAp19 may have a biological role in the regulation of MASP-2 protein expression and the lectin pathway activation route of complement. Through the use of a gene targeted mouse model for the deficiency of MAp19 (i.e. Map19−/−), the present inventors have shown that it is possible to inhibit lectin pathway activation and C4 deposition via the MASP-2 dependent lectin pathway, while leaving the classical pathway intact. The present invention thus suggests the use of MAp19 as a therapeutic target for inhibiting cellular injury associated with lectin-mediated alternate complement pathway activation, while leaving the classical (C1q-dependent) pathway component of the immune system intact.

The invention claimed is:

1. A method for production of an antibody directed against a human MASP-2 protein, the method comprising the step of introducing a human MASP-2 protein, or an immunogenic portion thereof, into a genetically modified mouse, wherein
   (i) the genetically modified mouse is homozygous for a null mutation that disrupts exons 10, 11 and 12 of the endogenous MASP-2 gene, wherein the endogenous MASP-2 polypeptide is not produced; or
   (ii) the genetically modified mouse is homozygous for a null mutation that disrupts exons 5, 10, 11 and 12 of the endogenous MASP-2 gene, wherein the endogenous MAS-2 polypeptide and the endogenous Map 19 polypeptide are not produced;

and wherein the genetically modified mouse lacks a lectin complement pathway response and retains a classical complement pathway response.

2. The method of claim 1, wherein all the endogenous MASP-2 gene sequences are absent from the genome of the genetically modified mouse.

* * * * *

UNITED STATES PATENT AND TRADEMARK OFFICE
CERTIFICATE OF CORRECTION

| | |
|---|---|
| PATENT NO. | : 10,660,317 B2 |
| APPLICATION NO. | : 15/348162 |
| DATED | : May 26, 2020 |
| INVENTOR(S) | : Teizo Fujita |

Page 1 of 2

It is certified that error appears in the above-identified patent and that said Letters Patent is hereby corrected as shown below:

On the Title Page

In Column 1, delete "(60) Continuation" and insert -- (63) Continuation --, therefor.

In Column 1, under "Related U.S. Application Data", Line 3, delete "filed as application No. PCT/GB2005/050086" and insert -- which is a 371 National Stage Entry of International PCT Application No. PCT/GB2005/050086, filed --, therefor.

In Column 2, item (57), under Abstract, Line 2, delete "mannan binding," and insert -- mannan-binding, --, therefor.

Page 3, in Column 1, item (56), under OTHER PUBLICATIONS, Line 4, delete "Structual" and insert -- Structural --, therefor.

In the Specification

In Column 1, Line 23, delete "mannan binding," and insert -- mannan-binding, --, therefor.

In Column 3, Line 27, delete "fibrinogen like" and insert -- fibrinogen-like --, therefor.

In Column 4, Line 15, delete "(2003)." and insert -- (2003)). --, therefor.

In Column 4, Line 36, delete "19 kDa" and insert -- 19kDa --, therefor.

In Column 7, Line 32, delete "site specific" and insert -- site-specific --, therefor.

In Column 8, Line 4, delete "gancyclovir" and insert -- ganciclovir --, therefor.

In Column 9, Line 42, delete "gancyclovir" and insert -- ganciclovir --, therefor.

Signed and Sealed this
Twenty-fourth Day of May, 2022

Katherine Kelly Vidal
*Director of the United States Patent and Trademark Office*

In Column 10, Line 32, delete "chimaeric animal." and insert -- chimeric animal. --, therefor.

In Column 10, Line 36, delete "Chimaeric animal." and insert -- Chimeric animal. --, therefor.

In Column 10, Line 43, delete "chimaeric animal." and insert -- chimeric animal. --, therefor.

In Column 16, Line 16, delete "MAp-19" and insert -- MAp 19 --, therefor.

In Column 19, Line 43, delete "(exon 1 to exon3)" and insert -- (exon1 to exon3) --, therefor.

In the Claims

In Column 30, Claim 1, Line 17, delete "MAS-2" and insert -- MASP-2 --, therefor.

SEQUENCE LISTING

```
<160> NUMBER OF SEQ ID NOS: 2

<210> SEQ ID NO 1
<211> LENGTH: 4960
<212> TYPE: DNA
<213> ORGANISM: Artificial sequence
<220> FEATURE:
<223> OTHER INFORMATION: Targeting construct

<400> SEQUENCE: 1
ccggacgtgg tggcgcatgc ctgtaatccc agctactcgg gaggctgagg caggagaatt      60
gctcgaaccc cggaggcaga ggtttggtgg ctcacacctg taatcccagc actttgcgag     120
gctgaggcag gtgcatcgct ttggctcagg agttcaagac cagcctgggc aacacaggga     180
gacccccatc tctacaaaaa acaaaaacaa atataaaggg gataaaaaaa aaaaaaagac     240
aagacatgaa tccatgagga cagagtgtgg aagaggaagc agcagcctca aagttctgga     300
agctggaaga acagataaac aggtgtgaaa taactgcctg gaaagcaact tcttttttttt    360 ttttttttttt tttgaggtgg agtctcactc tgtcgtccag gctggagtgc agtggtgcga     420
tctcggatca ctgcaacctc cgcctcccag gctcaagcaa ttctcctgcc tcagcctccc     480
gagtagctgg gattataagt gcgcgctgcc acacctggat gattttttgta tttttagtag    540 agatgggatt tcaccatgtt ggtcaggctg gtctcaaact cccaacctcg tgatccaccc     600
accttggcct cccaaagtgc tgggattaca ggtataagcc accgagccca gccaaaagcg     660
acttctaagc ctgcaaggga atcgggaatt ggtggcacca ggtccttctg acagggttta     720
agaaattagc cagcctgagg ctgggcacgg tggctcacac ctgtaatccc agcactttgg     780
gaggctaagg caggtggatc acctgagggc aggagttcaa gaccagcctg accaacatgg     840
agaaacccca tccctaccaa aaataaaaaa ttagccaggt gtggtggtgc tcgcctgtaa     900
tcccagctac ttgggaggct gaggtgggag gattgcttga acacaggaag tagaggctgc     960
agtgagctat gattgcagca ctgcactgaa gccgggcaa cagaacaaga tccaaaaaaa    1020
```

```
agggagggggt gaggggcaga gccaggattt gtttccaggc tgttgttacc taggtccgac    1080
tcctggctcc cagagcagcc tgtcctgcct gcctggaact ctgagcaggc tggagtcatg    1140
gagtcgattc ccagaatccc agagtcaggg aggctggggg caggggcagg tcactggaca    1200
aacagatcaa aggtgagacc agcgtagggc tgcagaccag gccaggccag ctggacgggc    1260
acaccatgag gtaggtgggc gcccacagcc tccctgcagg gtgtggggtg ggagcacagg    1320
cctgggccct caccgcccct gccctgccca taggctgctg accctcctgg gccttctgtg    1380
tggctcggtg gccaccccct tgggcccgaa gtggcctgaa cctgtgttcg ggcgcctggc    1440 atccccggc tttccagggg agtatgccaa tgaccaggag cggcgctgga ccctgactgc    1500
accccccggc taccgcctgc gcctctactt cacccacttc gacctggagc tctcccacct    1560
ctgcgagtac gacttcgtca aggtgccgtc aggacgggag ggctgggtt tctcagggtc    1620 gggggtccc caaggagtag ccagggttca gggacacctg ggagcagggg ccaggcttgg    1680
ccaggaggga gatcaggcct gggtcttgcc ttcactccct gtgacacctg accccacagc    1740
tgagctcggg ggccaaggtg ctggccacgc tgtgcgggca ggagagcaca gacacggagc    1800
gggcccctgg caaggacact ttctactcgc tgggctccag cctggacatt accttccgct    1860
ccgactactc caacgagaag ccgttcacgg ggttcgaggc cttctatgca gccgagggtg    1920
agccaagagg ggtcctgcaa catctcagtc tgcgcagctg gctgtggggg taactctgtc    1980
ttaggccagg cagccctgcc ttcagtttcc ccaccttttcc cagggcaggg gagaggcctc    2040
tggcctgaca tcatccacaa tgcaaagacc aaaacagccg tgacctccat tcacatgggc    2100
tgagtgccaa ctctgagcca gggatctgag gacagcatcg cctcaagtga cgcagggact    2160
ggccgggcgc agcagctcac gcctgtaatt ccagcacttt gggaggccga ggctggctga    2220
tcatttgagg tcaggagttc aaggccagcc agggcaacac ggtgaaactc tatctccact    2280
aaaactacaa aaattagctg ggcgtggtgg tgcgcacctg gaatcccagc tactagggag    2340
gctgaggcag gagaattgct tgaacctgcg aggtggaggc tgcagtgaac agagattgca    2400
ccactacact ccagcctggg cgacagagct agactccgtc tcaaaaaaca aaaaacaaaa    2460
acgacgcagg ggccgagggc cccatttaca gctgacaaag tggggccctg ccagcgggag    2520
cgctgccagg atgtttgatt tcagatccca gtccctgcag agaccaactg tgtgacctct    2580
ggcaagtggc tcaatttctc tgctccttag gaagctgctg caagggttca gcgctgtagc    2640
cccgccccct gggtttgatt gactcccctc attagctggg tgacctcggg ccggacactg    2700
aaactcccac tggtttaaca gaggtgatgt ttgcatcttt ctcccagcgc tgctgggagc    2760
ttgcagcgac cctaggcctg taaggtgatt ggcccggcac cagtcccgca ccctagacag    2820
gacgaggcct cctctgaggt ccactctgag gtcatggatc tcctggggag agtccaggct    2880
ggatcccgcc tctttccctc ctgacggcct gcctggccct gcctctcccc cagacattga    2940
cgagtgccag gtgccccgg gagaggcgcc caccctgcgac caccactgcc acaaccacct    3000
gggcggtttc tactgctcct gccgcgcagg ctacgtcctg caccgtaaca agcgcacctg    3060
ctcagccctg tgctccggcc aggtcttcac ccagaggtct ggggagctca gcagccctga    3120
atacccacgg ccgtatccca aactctccag ttgcacttac agcatcagcc tggaggaggg    3180
gttcagtgtc attctggact ttgtggagtc cttcgatgtg gagacacacc ctgaaaccct    3240
gtgtccctac gactttctca agattcaaac agacagagaa gaacatggcc cattctgtgg    3300
gaagacattg ccccacagga ttgaaacaaa aagcaacacg gtgaccatca cctttgtcac    3360
```

```
agatgaatca ggagaccaca caggctggaa gatccactac acgagcacag cgcacgcttg    3420
cccttatccg atggcgccac ctaatggcca cgtttcacct gtgcaagcca aatacatcct    3480
gaaagacagc ttctccatct tttgcgagac tggctatgag cttctgcaag gtcacttgcc    3540
cctgaaatcc tttactgcag tttgtcagaa agatggatct tgggaccggc caatgcccgc    3600
gtgcagcatt gttgactgtg gccctcctga tgatctaccc agtggccgag tggagtacat    3660
cacaggtcct ggagtgacca cctacaaagc tgtgattcag tacagctgtg aagagacctt    3720
ctacacaatg aaagtgaatg atggtaaata tgtgtgtgag gctgatggat tctggacgag    3780
ctccaaagga gaaaaatcac tcccagtctg tgagcctgtt tgtggactat cagcccgcac    3840
aacaggaggg cgtatatatg gagggcaaaa ggcaaaacct ggtgattttc cttggcaagt    3900
cctgatatta ggtggaacca cagcagcagg tgcacttttta tatgacaact gggtcctaac    3960
agctgctcat gccgtctatg agcaaaaaca tgatgcatcc gccctggaca ttcgaatggg    4020
caccctgaaa agactatcac ctcattatac acaagcctgg tctgaagctg ttttttataca    4080 tgaaggttat actcatgatg ctggctttga caatgacata gcactgatta aattgaataa    4140
caaagttgta atcaatagca acatcacgcc tatttgtctg ccaagaaaag aagctgaatc    4200
ctttatgagg acagatgaca ttggaactgc atctggatgg ggattaaccc aaaggggttt    4260
tcttgctaga aatctaatgt atgtcgacat accgattgtt gaccatcaaa aatgtactgc    4320
tgcatatgaa aagccaccct atccaagggg aagtgtaact gctaacatgc tttgtgctgg    4380
cttagaaagt gggggcaagg acagctgcag aggtgacagc ggaggggcac tggtgtttct    4440
agatagtgaa acagagaggt ggtttgtggg aggaatagtg tcctggggtt ccatgaattg    4500 tgggaagca ggtcagtatg gagtctacac aaaagttatt aactatattc cctggatcga    4560
gaacataatt agtgattttt aacttgcgtg tctgcagtca aggattcttc attttttagaa    4620 atgcctgtga agaccttggc agcgacgtgg ctcgagaagc attcatcatt actgtggaca    4680
tggcagttgt tgctccaccc aaaaaaaacag actccaggtg aggctgctgt catttctcca    4740
cttgccagtt taattccagc cttacccatt gactcaaggg gacataaacc acgagagtga    4800
cagtcatctt tgcccaccca gtgtaatgtc actgctcaaa ttacatttca ttaccttaaa    4860
aagccagtct cttttcatac tggctgttgg catttctgta aactgcctgt ccatgctctt    4920
tgtttttaaa cttgttctta ttgaaaaaaa aaaaaaaaa                           4960

<210> SEQ ID NO 2
<211> LENGTH: 3236
<212> TYPE: DNA
<213> ORGANISM: Artificial sequence
<220> FEATURE:
<223> OTHER INFORMATION: Targeting construct

<400> SEQUENCE: 2
ccggacgtgg tggcgcatgc ctgtaatccc agctactcgg gaggctgagg caggagaatt      60
gctcgaaccc cggaggcaga ggtttggtgg ctcacacctg taatcccagc actttgcgag     120
gctgaggcag gtgcatcgct ttggctcagg agttcaagac cagcctgggc aacacaggga     180 gaccccatc tctacaaaaa acaaaaacaa atataaaggg gataaaaaaa aaaaaaagac      240
aagacatgaa tccatgagga cagagtgtgg aagaggaagc agcagcctca agttctggaa     300
agctggaaga acagataaac aggtgtgaaa taactgcctg gaaagcaact tcttttttt     360 tttttttttt tttgaggtgg agtctcactc tgtcgtccag gctggagtgc agtggtgcga     420
tctcggatca ctgcaacctc cgcctcccag gctcaagcaa ttctcctgcc tcagcctccc     480
```

```
gagtagctgg gattataagt gcgcgctgcc acacctggat gattttgta tttttagtag    540
agatgggatt tcaccatgtt ggtcaggctg gtctcaaact cccaacctcg tgatccaccc    600
accttggcct cccaaagtgc tgggattaca ggtataagcc accgagccca gccaaaagcg    660
acttctaagc ctgcaaggga atcgggaatt ggtggcacca ggtccttctg cagggttta    720
agaaattagc cagcctgagg ctgggcacgg tggctcacac ctgtaatccc agcactttgg    780
gaggctaagg caggtggatc acctgagggc aggagttcaa gaccagcctg accaacatgg    840
agaaacccca tccctaccaa aaataaaaaa ttagccaggt gtggtggtgc tcgcctgtaa    900
tcccagctac ttgggaggct gaggtgggag gattgcttga acacaggaag tagaggctgc    960
agtgagctat gattgcagca ctgcactgaa gccgggcaa cagaacaaga tccaaaaaaa   1020
agggagggt gaggggcaga gccaggattt gtttccaggc tgttgttacc taggtccgac   1080
tcctggctcc cagagcagcc tgtcctgcct gcctggaact ctgagcaggc tggagtcatg   1140
gagtcgattc ccagaatccc agagtcaggg aggctggggg caggcagg tcactggaca   1200
aacagatcaa aggtgagacc agcgtagggc tgcagaccag gccaggccag ctggacgggc   1260
acaccatgag gtaggtgggc gcccacagcc tccctgcagg gtgtggggtg ggagcacagg   1320
cctgggccct caccgccct gccctgccca taggctgctg accctcctgg gccttctgtg   1380
tggctcggtg gccaccccct tgggcccgaa gtggcctgaa cctgtgttcg ggcgcctggc   1440
atccccggc tttccagggg agtatgccaa tgaccaggag cggcgctgga ccctgactgc   1500
acccccggc taccgcctgc gcctctactt cacccactc gacctggagc tctcccacct   1560
ctgcgagtac gacttcgtca aggtgccgtc aggacgggag ggctgggtt tctcagggtc   1620
gggggtccc caaggagtag ccagggttca gggacacctg ggagcagggg ccaggcttgg   1680
ccaggaggga gatcaggcct gggtcttgcc ttcactccct gtgacacctg accccacagc   1740
tgagctcggg ggccaaggtg ctggccacgc tgtgcgggca ggagagcaca gacacggagc   1800
gggcccctgg caaggacact ttctactcgc tgggctccag cctggacatt accttccgct   1860
ccgactactc caacgagaag ccgttcacgg ggttcgaggc cttctatgca gccgagggtg   1920
agccaagagg ggtcctgcaa catctcagtc tgcgcagctg gctgtggggg taactctgtc   1980
ttaggccagg cagccctgcc ttcagtttcc ccacctttcc cagggcaggg gagaggcctc   2040
tggcctgaca tcatccacaa tgcaaagacc aaaacagccg tgacctccat tcacatgggc   2100
tgagtgccaa ctctgagcca gggatctgag gacagcatcg cctcaagtga cgcagggact   2160
ggccgggcgc agcagctcac gcctgtaatt ccagcacttt ggaggccga ggctggctga   2220
tcatttgagg tcaggagttc aaggccagcc agggcaacac ggtgaaactc tatctccact   2280
aaaactacaa aaattagctg gcgtggtgg tgcgcacctg gaatcccagc tactagggag   2340
gctgaggcag gagaattgct tgaacctgcg aggtggaggc tgcagtgaac agagattgca   2400
ccactacact ccagcctggg cgacagagct agactccgtc tcaaaaaaca aaaacaaaa   2460
acgacgcagg ggccgagggc cccatttaca gctgacaaag tggggccctg ccagcgggag   2520
cgctgccagt atgtttgatt tcagatccca gtccctgcag agaccaactg tgtgacctct   2580
ggcaagtggc tcaatttctc tgctccttag gaagctgctg caagggttca gcgctgtagc   2640
cccgcccct gggtttgatt gactcccctc attagctggg tgacctcggg ccggacactg   2700
aaactcccac tggtttaaca gaggtgatgt ttgcatcttt ctcccagcgc tgctgggagc   2760
ttgcagcgac cctaggcctg taaggtgatt ggcccggcac cagtcccgca ccctagacag   2820
```

```
-continued gacgaggcct cctctgaggt ccactctgag gtcatggatc tcctgggagg agtccaggct    2880
ggatcccgcc tctttccctc ctgacggcct gcctggccct gcctctcccc cagacattga    2940
cgagtgccag gtggcccggg gagaggcgcc cacctgcgac caccactgcc acaaccacct    3000
gggcggtttc tactgctcct gccgcgcagg ctacgtcctg caccgtaaca agcgcacctg    3060
ctcagagcag agcctctagc ctcccctgga gctccggctg cccagcaggt cagaagccag    3120
agccagcctg ctggcctcag ctccgggttg ggctgagatg ctgtgcccca actcccattc    3180
acccaccatg gacccaataa taaacctggc cccaccccaa aaaaaaaaaa aaaaaa        3236
```